United States Patent
Osoegawa

(10) Patent No.: US 11,389,072 B2
(45) Date of Patent: Jul. 19, 2022

(54) BLOOD PRESSURE MEASUREMENT CUFF AND SPHYGMOMANOMETER

(71) Applicant: OMRON HEALTHCARE Co., Ltd., Kyoto (JP)

(72) Inventor: Nobuhiko Osoegawa, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 643 days.

(21) Appl. No.: 15/685,947

(22) Filed: Aug. 24, 2017

(65) Prior Publication Data

US 2017/0347893 A1 Dec. 7, 2017

Related U.S. Application Data

(63) Continuation of application No. PCT/JP2015/082504, filed on Nov. 19, 2015.

(30) Foreign Application Priority Data

Feb. 27, 2015 (JP) .............................. JP2015-039252

(51) Int. Cl.
*A61B 5/022* (2006.01)
*A61B 5/0225* (2006.01)
(Continued)

(52) U.S. Cl.
CPC ............ *A61B 5/022* (2013.01); *A61B 5/0225* (2013.01); *A61B 5/0245* (2013.01);
(Continued)

(58) Field of Classification Search
CPC ..... B25B 5/068; A61B 5/02141; A61B 5/022; A61B 5/21; A61B 17/10; A61B 5/02233;
(Continued)

(56) References Cited

U.S. PATENT DOCUMENTS

| 714,850 A | * | 12/1902 | Zimmermann | ....... A61F 2/0054 128/885 |
| 1,748,227 A | * | 2/1930 | Hyams | .................. A61F 2/0054 606/157 |

(Continued)

FOREIGN PATENT DOCUMENTS

| CN | 203576485 U | 5/2014 |
| JP | H4-51916 U | 5/1992 |

(Continued)

OTHER PUBLICATIONS

International Search Report issued in corresponding Application No. PCT/JP2015/082504, dated Feb. 9, 2016 (5 pages).

(Continued)

*Primary Examiner* — Alex M Valvis
*Assistant Examiner* — Chanel J Jhin
(74) *Attorney, Agent, or Firm* — Osha Bergman Watanabe & Burton LLP

(57) ABSTRACT

A blood pressure measurement cuff includes a clamp mechanism that sandwiches a measurement site. The clamp mechanism includes a first clamp portion having a shape that is curved along a first half of the measurement site and a second clamp portion having a shape that is curved along a second half of the measurement site. The slide hole is formed penetrating through one end portion of the first clamp portion. The slide bar extends from the one end portion of the second clamp portion and into the slide hole, fits therein, and slides with friction with respect to the slide hole. The slide hole and the slide bar are curved so as to protrude on a side near other end portions of the first clamp portion and the second clamp portion.

11 Claims, 15 Drawing Sheets

(51) Int. Cl.
*A61B 5/024* (2006.01)
*A61B 5/0245* (2006.01)
*A61B 5/021* (2006.01)
*A61B 5/00* (2006.01)
*A61B 5/02* (2006.01)

(52) U.S. Cl.
CPC ...... *A61B 5/02141* (2013.01); *A61B 5/02233* (2013.01); *A61B 5/02422* (2013.01); *A61B 5/02427* (2013.01); *A61B 5/02007* (2013.01); *A61B 5/681* (2013.01)

(58) Field of Classification Search
CPC .............. A61B 5/0225; A61B 5/02422; A61B 5/02427; A61B 5/0245; A61B 5/02007; A61B 5/681
USPC ........................................................ 600/490
See application file for complete search history.

(56) References Cited

U.S. PATENT DOCUMENTS

| | | | | |
|---|---|---|---|---|
| 3,146,777 | A * | 9/1964 | Lee | A61B 5/022 600/496 |
| 3,147,754 | A * | 9/1964 | Koessler | A61F 2/0054 128/885 |
| 3,517,661 | A * | 6/1970 | Buffington | A61B 5/0285 600/501 |
| 4,994,019 | A * | 2/1991 | Fernandez | A61F 2/0036 600/30 |
| 5,161,787 | A * | 11/1992 | Hobday | B25B 5/06 269/166 |
| 5,509,888 | A * | 4/1996 | Miller | A61F 2/0036 600/29 |
| 5,823,972 | A * | 10/1998 | McRae | A61B 5/205 600/573 |
| 2002/0111640 | A1* | 8/2002 | Krause | A61F 2/0054 606/151 |
| 2003/0004421 | A1* | 1/2003 | Ting | A61B 5/022 600/485 |
| 2004/0260163 | A1* | 12/2004 | Kron | A61B 5/6834 600/345 |
| 2005/0080345 | A1* | 4/2005 | Finburgh | A61B 5/021 600/485 |
| 2005/0085835 | A1* | 4/2005 | Rennich | A61F 2/0054 606/157 |
| 2005/0241651 | A1* | 11/2005 | Rennich | A61B 17/122 128/885 |
| 2005/0251183 | A1* | 11/2005 | Buckman | A61B 17/08 606/157 |
| 2005/0283087 | A1* | 12/2005 | Takazawa | A61B 5/022 600/500 |
| 2005/0288597 | A1* | 12/2005 | Kishimoto | A61B 5/022 600/499 |
| 2006/0079792 | A1* | 4/2006 | Finburgh | A61B 5/681 600/485 |
| 2008/0011310 | A1* | 1/2008 | Anderson | A61F 2/0054 128/885 |
| 2008/0091112 | A1* | 4/2008 | Kondo | A61B 5/022 600/485 |
| 2009/0204144 | A1* | 8/2009 | De Francesco | A61F 2/0054 606/201 |
| 2010/0314517 | A1* | 12/2010 | Patzer | A61M 5/1417 248/230.3 |
| 2011/0079946 | A1* | 4/2011 | Yang | B25B 5/166 269/88 |
| 2011/0190805 | A1* | 8/2011 | Huber | A61M 29/00 606/191 |
| 2013/0046191 | A1* | 2/2013 | Lin | A61B 5/02233 600/500 |
| 2015/0223923 | A1* | 8/2015 | Forsell | A61N 1/0521 600/30 |
| 2018/0279889 | A1* | 10/2018 | Lee | A61B 5/6824 |
| 2019/0125259 | A1* | 5/2019 | Huang | A61B 5/0205 |
| 2019/0274593 | A1* | 9/2019 | Peluso | A61B 5/333 |
| 2019/0343432 | A1* | 11/2019 | Harris | A61B 5/6826 |

FOREIGN PATENT DOCUMENTS

| | | | |
|---|---|---|---|
| JP | 200408240 A | 1/2004 | |
| JP | 201343084 A | 3/2013 | |
| JP | 2013158347 A | 8/2013 | |
| JP | 2015036041 * | 2/2015 | .......... A61F 2/0054 |
| TW | M371529 U | 1/2010 | |
| WO | 2014017975 A1 | 1/2014 | |

OTHER PUBLICATIONS

Written Opinion issued in corresponding Application No. PCT/JP2015/082504, dated Feb. 9, 2016 (3 pages).

Office Action issued in Chinese Application No. 2015800769562; dated Sep. 24, 2019 (18 pages).

* cited by examiner

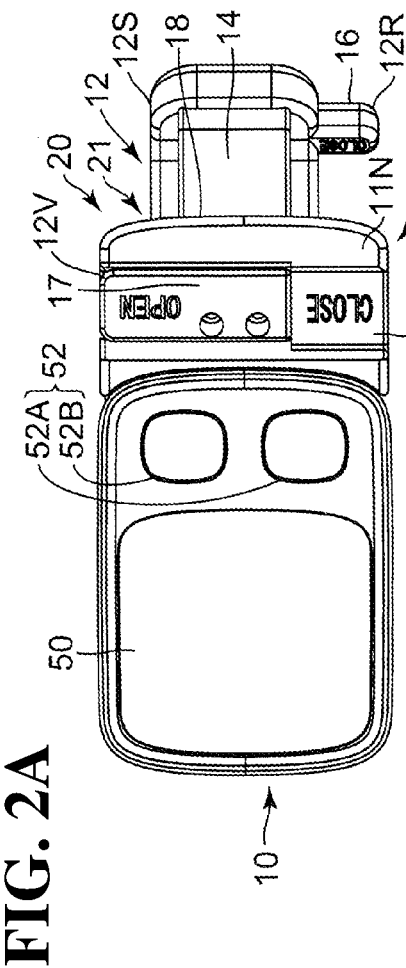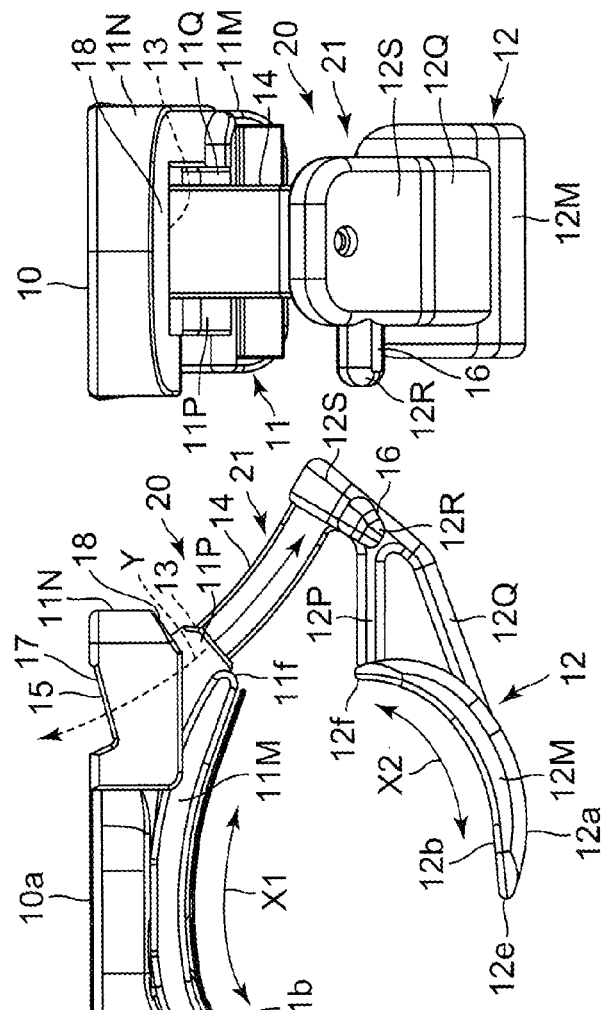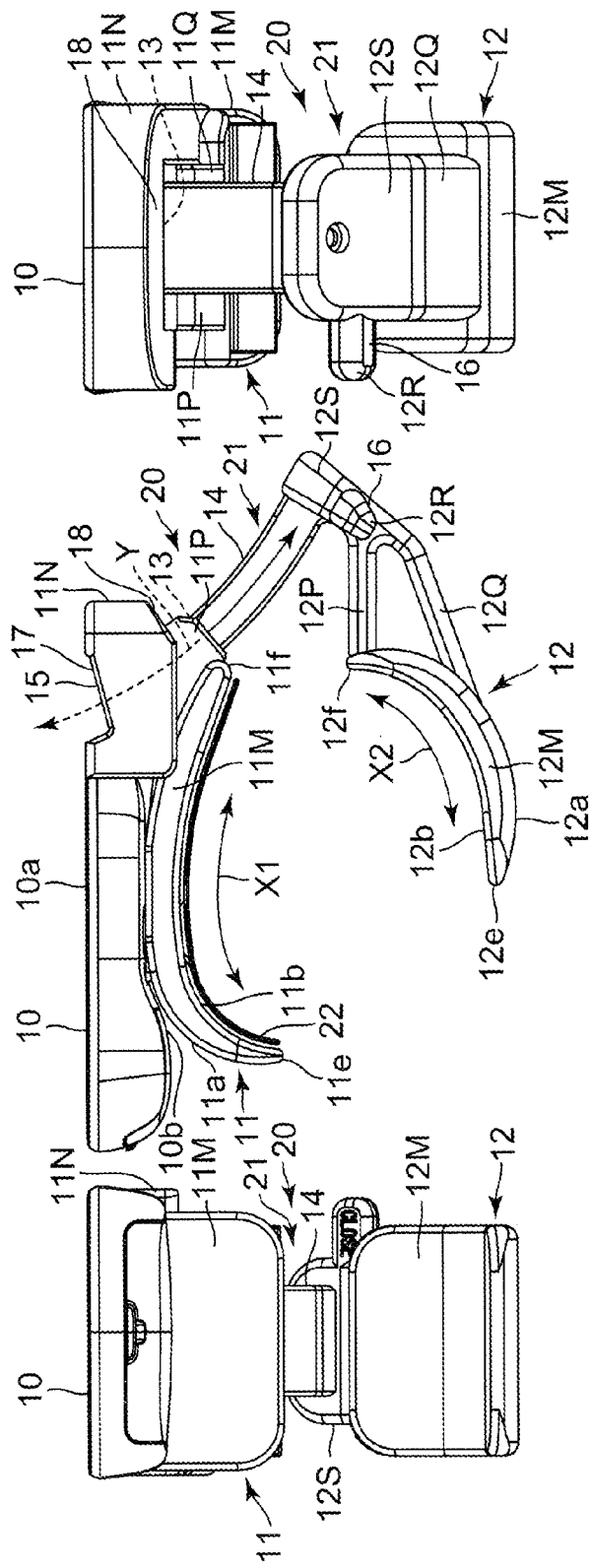

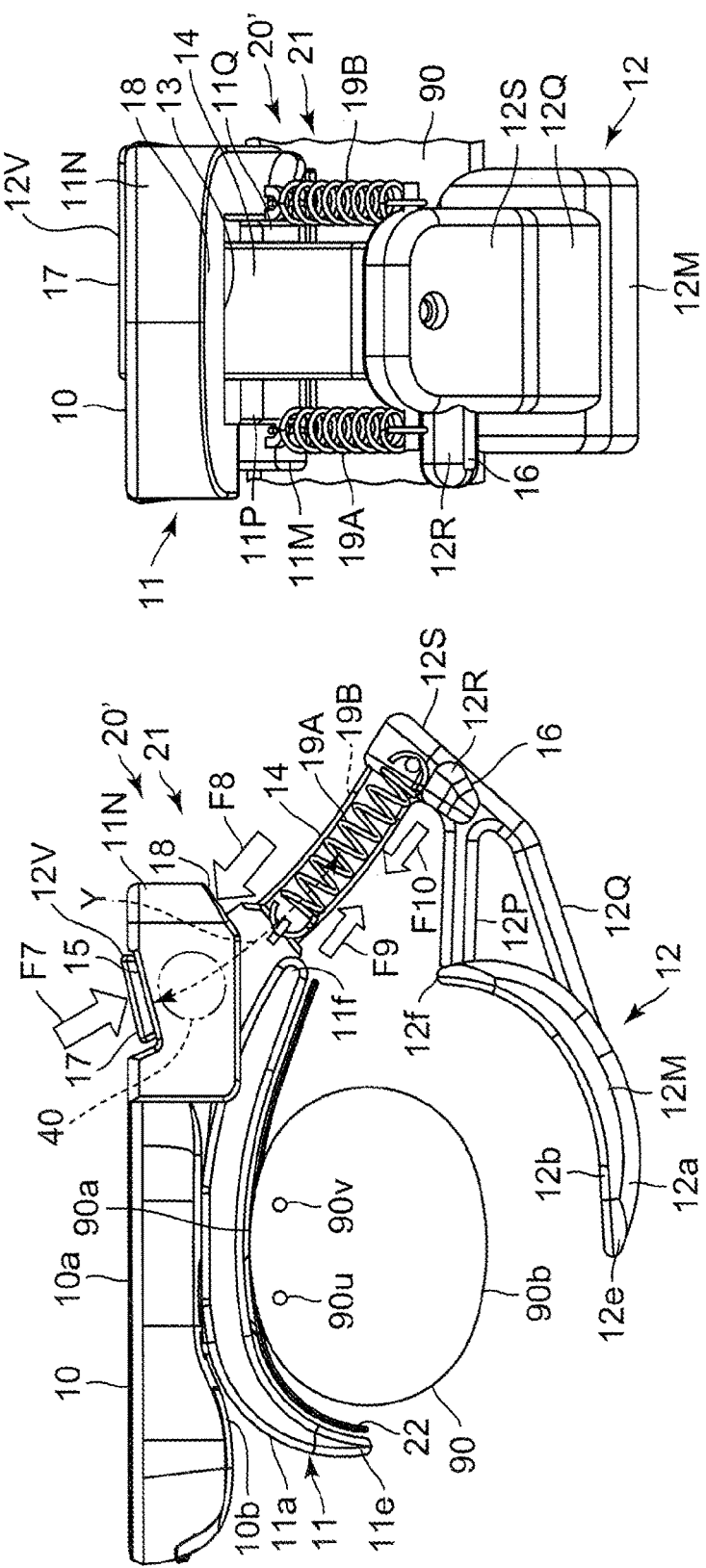

BLOOD PRESSURE MEASUREMENT CUFF AND SPHYGMOMANOMETER

TECHNICAL FIELD

One or more embodiments of the present invention relate to a blood pressure measurement cuff, and more specifically relates to a blood pressure measurement cuff having a clamp mechanism that sandwiches a measurement site.

One or more embodiments of the present invention relate to a blood pressure monitor including such a blood pressure measurement cuff.

BACKGROUND ART

Conventionally, as disclosed in Patent Document 1 (JP H4-51916U) for example, an auxiliary hemostasis tool for an arm is known which includes a lower-side fixed plate, an adjuster scale that extends in a vertical direction and is provided in a standing manner on the lower-side fixed plate, an adjuster portion provided on the adjuster scale so as to be able to slide vertically, an upper-side fixed plate that extends parallel to the lower-side fixed plate from the adjuster portion, and a compression end provided below the leading end of the upper-side fixed plate. The adjuster portion can be fixed to the adjuster scale with a fixing screw.

With this auxiliary hemostasis tool, in order to compress the arm, a procedure is undertaken in which
i) the fixing screw is loosened,
ii) the adjuster portion is slid upward along the adjuster scale to open the gap between the lower-side fixed plate and the compression end located thereabove,
iii) the arm is passed through the gap between the lower-side fixed plate and the compression end and positioned,
iv) the adjuster portion is slid downward along the adjuster scale to narrow the gap between the lower-side fixed plate and the compression end, and
v) the fixing screw is refastened.

Thus, hemostasis is achieved by the arm being sandwiched between the lower-side fixed plate and the compression end.

CITATION LIST

Patent Literature

Patent Document 1: JP H4-51916U

SUMMARY OF INVENTION

It is thought that the configuration in which the measurement site is sandwiched (referred to as a "clamp mechanism") as with the above-described auxiliary hemostasis tool can also be applied to a blood pressure measurement cuff.

However, with the above-described auxiliary hemostasis tool, the five operations i) to v) described above are needed in order to compress the arm, which is problematic in that it is inconvenient.

In view of this, one or more embodiments of the present invention aim to provide a blood pressure measurement cuff having a clamp mechanism that sandwiches a measurement site, and can be attached with a simple operation.

The blood pressure measurement cuff according to one or more embodiments of the present invention is a blood pressure measurement cuff including a clamp mechanism that sandwiches a substantially bar-shaped measurement site, wherein the clamp mechanism includes: a first clamp portion having a shape that is curved along a first half of an outer circumferential surface of the measurement site so as to press the side of the first half; a second clamp portion having a shape that is curved along a second half opposite to the first half of the outer circumferential surface of the measurement site so as to press the side of the second half; a slide hole that is formed at one end portion in a circumferential direction of the first clamp portion so as to penetrate in a penetration direction intersecting with the circumferential direction; and a slide bar that extends from one end portion of the second clamp portion corresponding to the one end portion of the first clamp portion and into the slide hole of the first clamp portion, fits therein, and slides with friction with respect to the slide hole, wherein the slide hole and the slide bar are curved so as to protrude on a side near other end portions of the first clamp portion and the second clamp portion.

In the present specification, one "end portion" of the first clamp portion and one "end portion" of the second clamp portion indicate portions in certain regions including edges.

Also, the "other end portions" of the first clamp portion and the second clamp portion each refer to an end portion on a side opposite to that of the "one end portion" among both end portions in the circumferential direction.

Also, the "sliding" of the slide bar with respect to the slide hole is relative. In contrast to the above description, it can also be said that the slide hole (i.e., the first clamp portion) slides with respect to the slide bar.

The blood pressure measurement cuff according to one or more embodiments of the present invention is attached to the measurement site using the following operation. Note that at first, the gap between the first clamp portion and the second clamp portion is in the open state (state in which the slide hole is located on the leading end side of the slide bar and the gap between the first clamp portion 11M and the second clamp portion 12M is open).
(a) First, the measurement site is arranged between the first clamp portion and the second clamp portion.
(b) Next, the slide bar is slid with respect to the slide hole in a direction of closing the gap between the first clamp portion and the second clamp portion, whereby the measurement site is sandwiched between the first clamp portion and the second clamp portion (the state in which the measurement site is thus sandwiched is called the "attached state").

The blood pressure measurement cuff is thus attached to the measurement site using two operations, namely the arranging operation (a) and the closing operation (b). Accordingly, the blood pressure measurement cuff can be attached using a simpler operation compared to the conventional example (in which five operations are needed).

In the above-described attached state, a fluid bladder provided along the inner circumferential surface of the first clamp portion for example is inflated for blood pressure measurement, and even if a force in the direction of relatively opening the gap between the inner circumferential surface of the first clamp portion and the inner circumferential surface of the second clamp portion is applied, a moment is applied from the slide hole to the slide bar and the frictional force increases. As a result, the first clamp portion does not easily open with respect to the second clamp portion (and the measurement site), and the above-described attached state is maintained.

Also, with this blood pressure measurement cuff, the slide hole and the slide bar are curved so as to protrude on the side near the other end portions of the first clamp portion and the second clamp portion. Accordingly, in the open state, the gap between the other end portion of the first clamp portion and the other end portion of the second clamp portion is open more widely in comparison to the case in which the slide hole and the slide bar are straight. As a result, the arranging operation (a), or in other words, the operation of arranging the measurement site between the first clamp portion and the second clamp portion, is easier.

After blood pressure measurement (a later-described operation for blood pressure measurement is denoted as (c)), the blood pressure measurement cuff is removed from the attached state using the following operation.

(d) The slide bar is slid with respect to the slide hole in the direction of opening the gap between the first clamp portion and the second clamp portion, whereby the gap between the first clamp portion and the second clamp portion is set to the open state.

(e) Next, the measurement site is removed from between the first clamp portion and the second clamp portion.

Note that since there is friction between the slide hole and the slide bar, it is easy to keep the blood pressure measurement cuff in the state in which the gap between the first clamp portion 11M and the second clamp portion 12M is open (open state). Note that the blood pressure measurement cuff may also be kept in a state in which the gap between the first clamp portion and the second clamp portion is closed (closed state). In this case, when the blood pressure measurement cuff is to be used, an operation of opening the gap between the first clamp portion and the second clamp portion is added before the above-described arranging operation (a).

With a blood pressure measurement cuff according to an embodiment, a fluid bladder that is to be inflated during blood pressure measurement is provided along one or both of an inner circumferential surface of the first clamp portion and an inner circumferential surface of the second clamp portion.

With the blood pressure measurement cuff according to the embodiment, in the attached state, the fluid bladder is inflated during blood pressure measurement. Accordingly, an artery passing through the measurement site is compressed, and blood pressure measurement is executed smoothly.

With a blood pressure measurement cuff according to an embodiment, a first pressing region for placing a finger is formed adjacent to the slide hole on the outer circumferential surface side of the one end portion of the first clamp portion, and a second pressing region for placing a finger is formed at a position corresponding to the first pressing region on the outer circumferential surface side of the one end portion of the second clamp portion.

For example, the measurement site belongs to the left half of the measurement subject's body (e.g., the left wrist, left upper arm, or the like). With the blood pressure measurement cuff of the embodiment, at the time of the arranging operation (a), the slide hole and the slide bar are arranged on a side near the center of the body of the measurement subject, and in this case, on a side near the right hand, in the periphery of the measurement site. In that case, the measurement subject can close the gap between the first clamp portion and the second clamp portion by pinching the first pressing region and the second pressing region with the thumb and another finger of the right hand so that they are brought close to each other. At this time, the first pressing region is formed adjacent to the slide hole and the second pressing region is formed at a position corresponding to the first pressing region, and therefore the pressing force applied by the slide hole to the slide bar is relatively small. By contrast, the pressing force applied by the slide bar to the slide hole is relatively small. Accordingly, the frictional force between the slide hole and the slide bar is also relatively small. As a result, the measurement subject can easily close the gap between the first clamp portion and the second clamp portion. In other words, the closing operation (b) can be easily performed with the right hand (one hand).

With a blood pressure measurement cuff according to an embodiment, a third pressing region for placing a finger is formed on a leading end of the slide bar, and a fourth pressing region for placing a finger is formed adjacent to the slide hole on the inner circumferential surface side of the one end portion of the first clamp portion.

With the blood pressure measurement cuff of the embodiment, at the time of the opening operation (d), the measurement subject can open the gap between the first clamp portion and the second clamp portion by pinching the third pressing region and the fourth pressing region with the thumb and another finger of one hand so as to bring them close to each other. At this time, the third pressing region is formed on the leading end of the slide bar and the fourth pressing region is formed adjacent to the slide hole, and therefore the pressing force applied by the slide hole to the slide bar is relatively small. Accordingly, the frictional force between the slide hole and the slide bar is also relatively small. As a result, the measurement subject can easily open the gap between the first clamp portion and the second clamp portion. In other words, the opening operation (d) can be performed easily with one hand.

With a blood pressure measurement cuff according to an embodiment, a cross section of the slide hole taken orthogonally to the penetration direction is substantially rectangular, and the shape of a cross section of the slide bar taken orthogonally to a direction in which the slide bar extends substantially matches the shape of the cross section of the slide hole.

Here, the cross section of the slide hole being "substantially rectangular" encompasses not only being a true rectangle, but also a case of being slightly deformed due to manufacturing variation or the like. Also, the shape of the cross section of the slide bar "substantially matching" the shape of the cross section of the slide hole encompasses not only being a true rectangle, but also a case in which chamfering is formed on a corner portion (in the cross section) of the slide bar, and a case of being slightly deformed due to manufacturing variation or the like.

With the blood pressure measurement cuff of the embodiment, at the time of the closing operation (b) or the opening operation (d), the first clamp portion and the second clamp portion move (slide) along the plane including the curved slide bar. In other words, since the slide bar that is rectangular in cross section fits into the slide hole that is rectangular in cross section, the first clamp portion is restricted from rotating about the slide bar. Accordingly, even if the operations (a) to (e) are repeated, after the closing operation (b), the first clamp portion and the second clamp portion will always oppose each other and enter a state in which the measurement site can be compressed.

With a blood pressure measurement cuff according to an embodiment, among edges constituting an exit/entrance of the slide hole on a side away from the second clamp portion in the penetration direction, a second edge on a side near the other end portion of the first clamp portion is at a position closer to the second clamp portion in the penetration direction than a first edge on a side away from the other end portion of the first clamp portion is, and/or among edges constituting an exit/entrance on a side near the second clamp portion of the slide hole in the penetration direction, a third edge on a side far from the other end portion of the first clamp portion is at a position farther from the second clamp portion in the penetration direction than a fourth edge on a side near the other end portion of the first clamp portion is.

With the blood pressure measurement cuff of the embodiment, in the attached state, the fluid bladder provided along the inner circumferential surface of the first clamp portion for example is inflated for blood pressure measurement, and when a force in a direction of relatively opening is applied between the inner circumferential surface of the first clamp portion and the inner circumferential surface of the second clamp portion, the pressing force applied by the inner surface of the slide hole to the slide bar increases. Specifically, when the inner circumferential surface of the first clamp portion is used as a point of effort and the second edge of the slide hole is used as a fulcrum, the third edge of the slide hole corresponds to the point of action. Here, with the blood pressure measurement cuff of the embodiment, the second edge is at a position closer to the second clamp portion in the penetration direction than the first edge is, and/or the third edge is at a position farther from the second clamp portion in the penetration direction than the fourth edge is. In other words, the distance (length of the arm of the moment) between the second edge that is the fulcrum and the third edge that is the point of action is relatively short. Accordingly, the pressing force that acts on the third edge that is the point of action (and the second edge that is the fulcrum) increases. As a result, the frictional force that acts between the slide hole and the slide bar increases. As a result, the first clamp portion is even less likely to open with respect to the second clamp portion (and the measurement site), and the above-described attached state is reliably maintained.

With a blood pressure measurement cuff according to an embodiment, curves are formed in cross sections of the first edge and the fourth edge so as to reduce friction, and cross sections of the second edge and the third edge are formed in right angles or acute angles so as to increase friction.

With the above-described closing operation (b), the pressing force applied by the inner surface of the slide hole to the slide bar acts mainly on the first edge and the fourth edge. Here, with the blood pressure measurement cuff of the embodiment, curves are formed in the cross sections of the first edge and the fourth edge so as to reduce friction. Accordingly, the closing operation (b) is more easily performed. Also, for example, in the attached state, the fluid bladder provided along the inner circumferential surface of the first clamp portion for example is inflated for blood pressure measurement, and when a force in a direction of relatively opening is applied between the inner circumferential surface of the first clamp portion and the inner circumferential surface of the second clamp portion, the pressing force applied by the inner surface of the slide hole to the slide bar acts mainly on the second edge and the third edge. Here, with the blood pressure measurement cuff of the embodiment, the cross sections of the second edge and the third edge are formed into right angles or acute angles so as to increase friction. Accordingly, the first clamp portion is even less likely to open with respect to the second clamp portion (and the measurement site), and the above-described attached state is reliably maintained.

With a blood pressure measurement cuff according to an embodiment, a dimension in the circumferential direction of the second clamp portion is set to be smaller than a dimension in the circumferential direction of the first clamp portion, and the penetration direction of the slide hole is directed outward in the circumferential direction with respect to the one end portion of the first clamp portion as the inner circumferential surface side is approached from the outer circumferential surface side of the first clamp portion.

With the blood pressure measurement cuff of the embodiment, for example, if the measurement site serving as a measurement target is thick, the dimension in the circumferential direction of the first clamp portion is set to be a dimension that completely covers a first half of the thick measurement site. The artery to be compressed passes through the first half. In this case, at the time of the arranging operation (a), the first half of the thick measurement site is arranged to as to oppose the inner circumferential surface of the first clamp portion. Note that due to the fact that the dimension in the circumferential direction of the second clamp portion is smaller than the dimension in the circumferential direction of the first clamp portion, in the attached state after the closing operation (b), the portion of the second half of the thick measurement site located far from the slide bar sometimes protrudes outward with respect to the other end portion of the second clamp portion, but if the fluid bladder is provided approximately in the entire region along the inner circumferential surface of the first clamp portion, blood pressure measurement will not be hindered. On the other hand, in the case where the measurement site serving as the measurement target is thin as well, at the time of the arranging operation (a), the first half of the thin measurement site is arranged facing the inner circumferential surface of the first clamp portion. At the time of the closing operation (b), as the second clamp portion relatively approaches the first clamp portion, the second clamp portion changes the region that faces from the one end portion to the other end portion of the first clamp portion while significantly moving approximately diagonally (also includes rotation of the orientation that accompanies the curves of the slide hole and the slide bar). Accordingly, the thin measurement site can be reliably sandwiched between the first clamp portion and the second clamp portion.

With a blood pressure measurement cuff according to an embodiment, a fluid bladder that is to be inflated during blood pressure measurement is provided in approximately the entire region along the inner circumferential surface of the first clamp portion, and an element that restricts swelling of an opposing portion of the fluid bladder is provided on an inner circumferential surface side of a portion adjacent to the one end portion of the second clamp portion.

In the case where the measurement site serving as the measurement target is thin, unless there is some contrivance, when the fluid bladder is inflated, the end portion of the fluid bladder on the side near the slide bar swells significantly toward the second clamp portion, and there is a possibility that blood pressure measurement will be hindered. Here, with the blood pressure measurement cuff of the embodiment, the inner circumferential surface side of the portion adjacent to the one end portion of the second clamp portion is provided with an element that restricts swelling of the opposing portion of the fluid bladder. Accordingly, the element restricts swelling of the opposing portion of the fluid bladder. As a result, blood pressure measurement is performed accurately and smoothly.

With a blood pressure measurement cuff according to an embodiment, an elastic member that applies a tensile force between the one end portion of the first clamp portion and the one end portion of the second clamp portion.

With the blood pressure measurement cuff of the embodiment, at the time of the closing operation, the gap between the first clamp portion and the second clamp portion is easily closed due to the tensile force of the elastic member. For example, if the tensile force of the elastic member is set to be larger than the frictional force between the slide hole and the slide bar, at the time of the closing operation, the measurement subject no longer needs to apply an external force for closing the gap between the first clamp portion and the second clamp portion. Also, in the attached state, due to the tensile force of the elastic member, the inner circumferential surface of the first clamp portion (or the fluid bladder) and the inner circumferential surface of the second clamp portion comes into close contact with the measurement site. Accordingly, blood pressure measurement is performed accurately and smoothly.

A blood pressure measurement cuff according to an embodiment includes a latch mechanism that keeps the first clamp portion and the second clamp portion in an open state.

With the blood pressure measurement cuff of the embodiment, the latch mechanism keeps the gap between the first clamp portion and the second clamp portion in the open state. Accordingly, the measurement subject can perform the arranging operation while the gap between the first clamp portion and the second clamp portion is kept in the open state. Note that after the arranging operation, the maintenance of the open state performed by the latch mechanism can be removed.

In another aspect, a blood pressure monitor according to one or more embodiments of the present invention includes: the blood pressure measurement cuff according to one or more embodiments of the present invention; and a main body with an element for blood pressure measurement built in.

With the blood pressure monitor according to one or more embodiments of the present invention, the blood pressure measurement cuff can be attached using a simple operation as described above. Accordingly, blood pressure measurement is performed smoothly.

Specifically, in the attached state resulting from the arranging operation (a) and the closing operation (b) being performed in sequence, (c) an operation switch provided in the main body for example is pressed and a blood pressure measurement start instruction is input to the main body. Accordingly, the fluid bladder provided along the inner circumferential surface of the first clamp portion for example is inflated, and blood pressure measurement is performed.

(d) After measurement ends, the slide bar is slid with respect to the slide hole in the direction of opening the gap between the first clamp portion and the second clamp portion, whereby the gap between the first clamp portion and the second clamp portion is set to the open state.

(e) The measurement site is removed from between the first clamp portion and the second clamp portion.

Thus, with the blood pressure monitor, blood pressure measurement is performed smoothly.

With a blood pressure monitor of an embodiment,
the main body is integrally attached to the blood pressure measurement cuff so as to cover the outer circumferential surface of the first clamp portion,
an operation switch for inputting a blood pressure measurement start instruction is provided in a region adjacent to the slide hole of the first clamp portion on the outer surface of the main body, and
a second pressing region for placing a finger is formed at a position corresponding to the operation switch on the outer circumferential surface side of the one end portion of the second clamp portion of the cuff.

For example, the measurement site belongs to the left half of the measurement subject's body (e.g., the left upper arm or the left wrist). With the blood pressure monitor of the embodiment, when performing the above-described arranging operation (a), the slide hole and the slide bar are arranged on a side near the center of the measurement subject's body, and in this case, on a side near the right hand, in the periphery of the measurement site. Moreover, an operation switch for inputting the blood pressure measurement start instruction is provided in a region of the outer surface of the main body that is adjacent to the slide hole of the first clamp portion. Accordingly, the measurement subject can easily close the gap between the first clamp portion and the second clamp portion by pinching the operation switch and the second pressing region with the thumb and another finger of the right hand such that they are brought close to each other. In other words, the closing operation (b) can be easily performed with one hand. Also, by performing the closing operation (b), it is possible to perform the measurement start instruction operation (c), or in other words, the operation of inputting the blood pressure measurement start instruction to the main body by pressing the operation switch provided on the main body. In other words, the closing operation (b) and the measurement start instruction operation (c) can be performed simultaneously. Accordingly, blood pressure measurement can be performed with a simple operation.

Advantageous Effects of the Invention

As is evident from the above description, the blood pressure measurement cuff according to one or more embodiments of the present invention can be attached using a simple operation.

Also, with the blood pressure monitor according to one or more embodiments of the present invention, the blood pressure measurement cuff can be attached using a simple operation.

BRIEF DESCRIPTION OF DRAWINGS

FIG. 2(C) is a diagram showing a view from the front of the blood pressure monitor shown in FIG. 1, FIG. 2(A) is a diagram showing a view from above of the blood pressure monitor shown in FIG. 2(C), FIG. 2(B) is a diagram showing a view from the left side of the blood pressure monitor shown in FIG. 2(C), and FIG. 2(D) is a diagram showing a view from the right side of the blood pressure monitor shown in FIG. 2(C).

FIG. 12(A) is a diagram showing an operation of opening the blood pressure measurement cuff shown in FIG. 11, and an operation of arranging the left wrist serving as the measurement site between the first clamp portion and the second clamp portion of the blood pressure measurement cuff. FIG. 12(B) is a diagram showing a view from the right side of the blood pressure monitor shown in FIG. 12(A).

DESCRIPTION OF EMBODIMENTS

Hereinafter, an embodiment of the invention will be described in detail with reference to the drawings.

Figure 1:
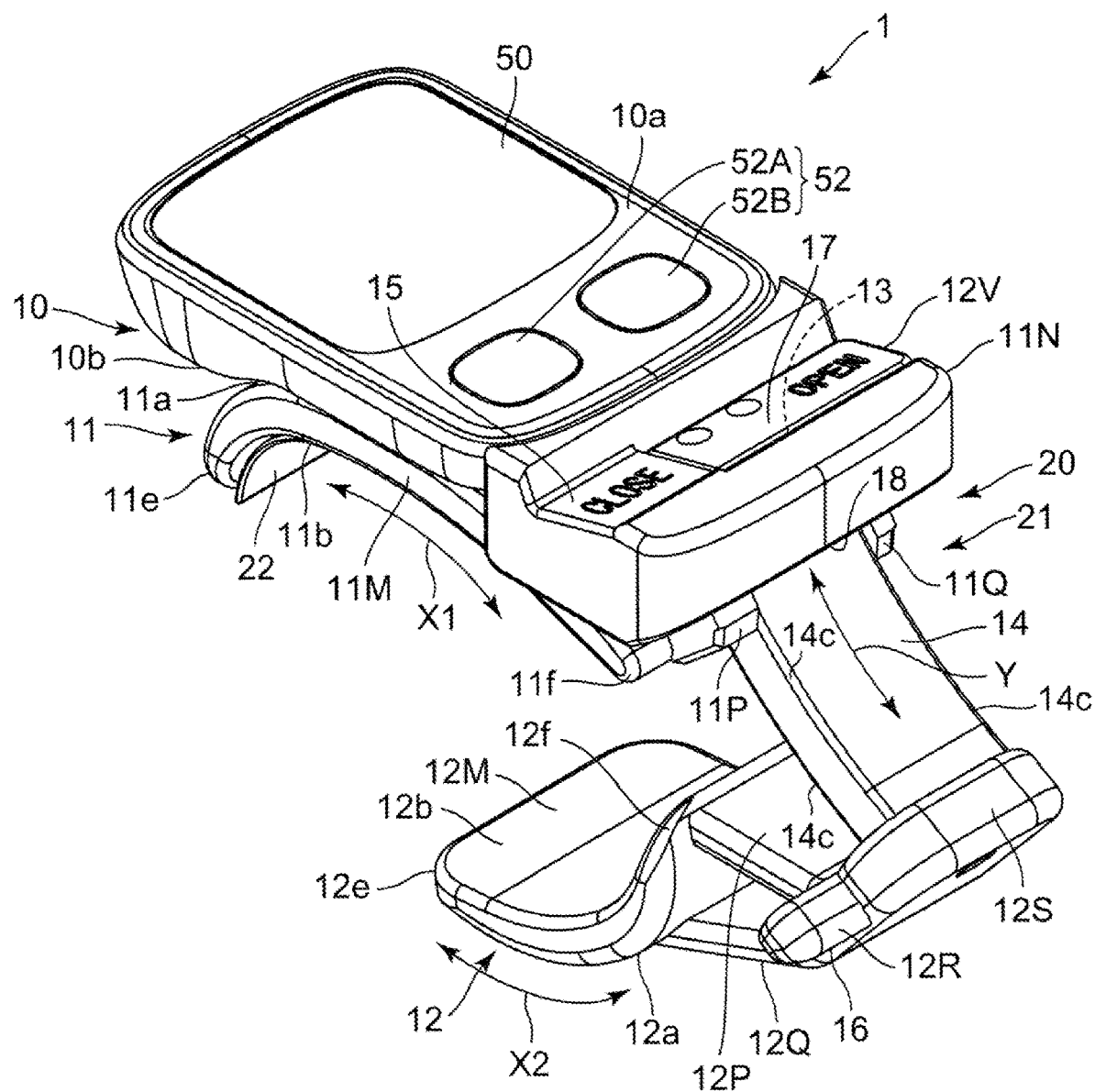
FIG. 1 is a perspective view showing the exterior of a blood pressure monitor that includes a blood pressure measurement cuff (in an open state) according to an embodiment of the invention.
Figure 3:
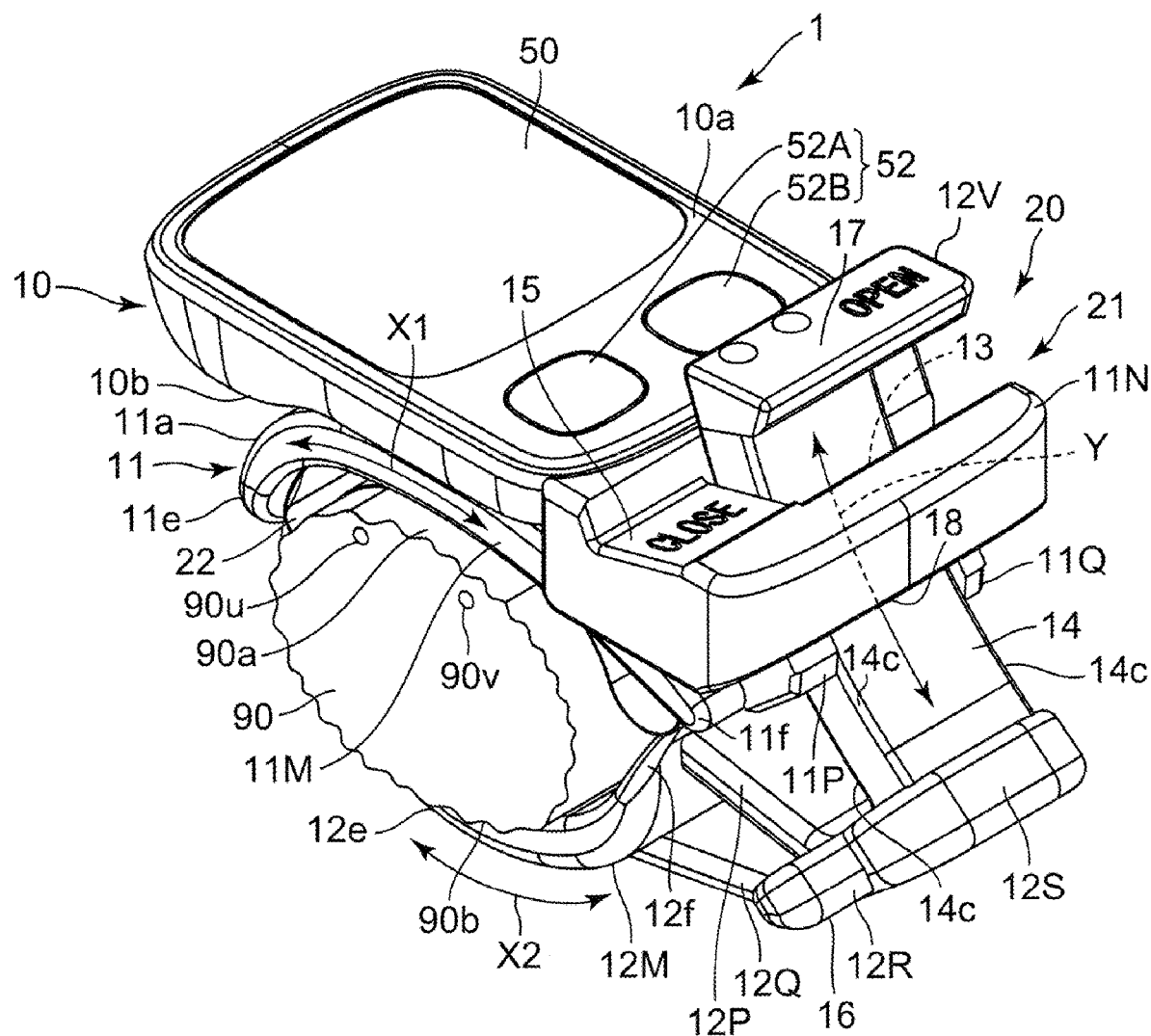
FIG. 3 is a perspective view showing a state (attached state) in which the blood pressure monitor including the blood pressure measurement cuff shown in FIG. 1 is attached to a left wrist serving as a measurement site.
Figure 4A:
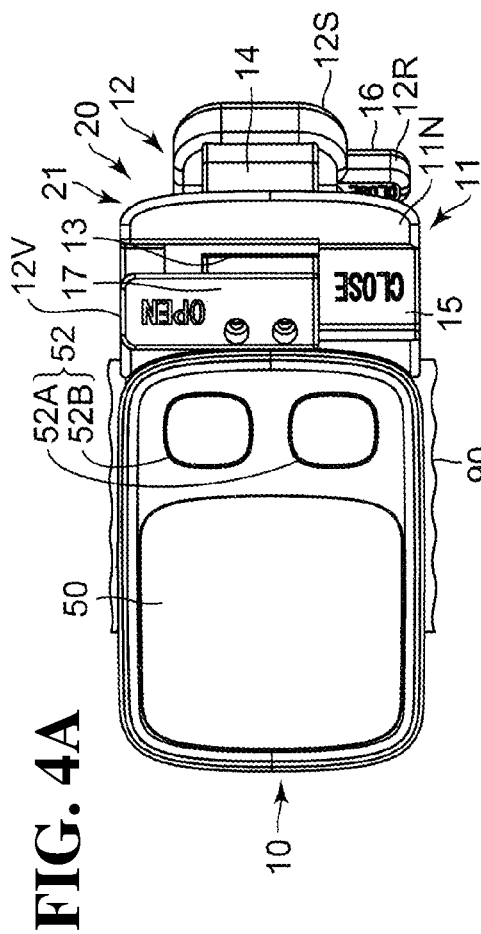
FIG. 4(A) is a diagram showing a view from above of the blood pressure monitor shown in FIG. 4(C)
Figure 4D:
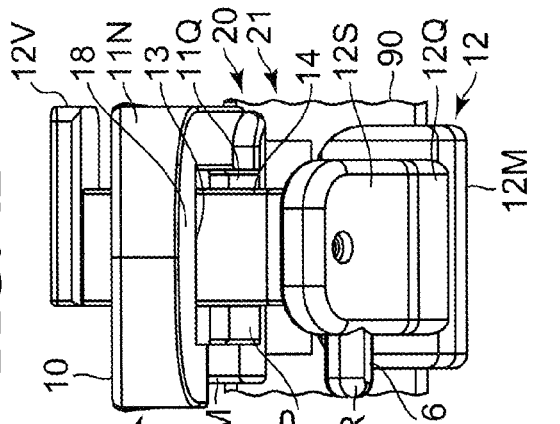
FIG. 4(D) is a diagram showing a view from the right side of the blood pressure monitor shown in FIG. 4(C).
Figure 4C:
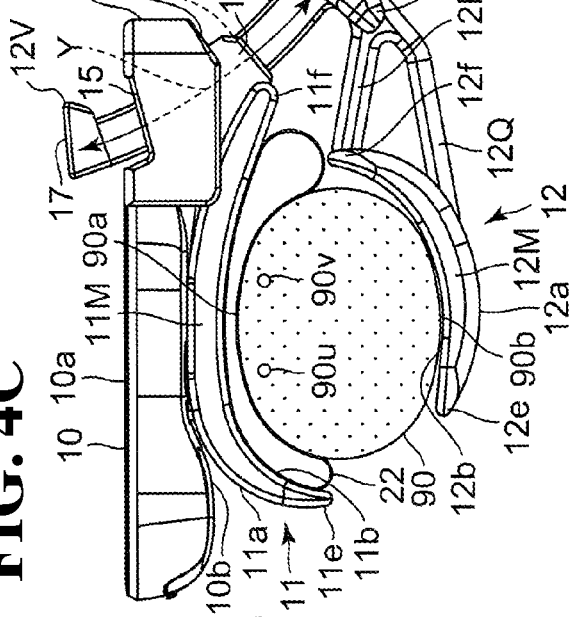
FIG. 4(C) is a diagram showing a view from the front of the blood pressure monitor shown in FIG. 3.
Figure 4B:
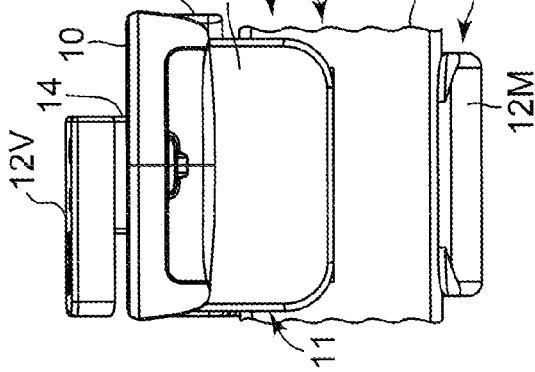
FIG. 4(B) is a diagram showing a view from the left side of the blood pressure monitor shown in FIG. 4(C)

FIG. 1 shows a perspective view of the exterior of a blood pressure monitor 1 including a blood pressure measurement cuff (in an open state) 20 according to an embodiment of the invention. Also, FIG. 2(C) shows a view from the front of the blood pressure monitor 1, FIG. 2(A) shows a view from above of the blood pressure monitor 1, FIG. 2(B) shows a view from the left side of the blood pressure monitor 1, and FIG. 2(D) shows a view from the right side of the blood pressure monitor 1. As shown in the drawings, the blood pressure monitor 1 integrally includes a blood pressure measurement cuff (hereinafter referred to as simply "cuff") 20 that includes a clamp mechanism 21, and a main body 10 in which an element for blood pressure measurement is installed. As shown in FIG. 3, the blood pressure monitor 1 is to be attached to an approximately bar-shaped left wrist 90 serving as a measurement site. The outer circumferential surface of the left wrist 90 includes a half 90a on the palm side serving as a first half, and a half 90b on the back side serving as a second half, which corresponds to the opposite side. Arteries 90u and 90v that are to be compressed at the time of blood pressure measurement pass through the vicinity of the half 90a on the palm side. Note that FIGS. 4(A) to 4(D) show the blood pressure monitor shown in FIG. 3 in correspondence with FIGS. 2(A) to 2(D).

As can be understood from FIGS. 1 and 2(C), the cuff 20 includes an upper-side member 11 to which the main body 10 is integrally attached, and a lower-side member 12 provided so as to be able to slide with respect to the upper-side member 11.

Note that "upper-side member" and "lower-side member" are names for the sake of convenience in the description, and in actuality, it is possible to use an orientation in which the upper-side member is on the lower side, and the lower-side member is on the upper side. The same follows for a later-described "left end portion" and "right end portion", and in actuality, it is possible to use an orientation in which the left end portion is on the right and the right end portion is on the left.

The upper-side member 11 includes a first clamp portion 11M that has a shape that is curved in a circumferential direction X1 along the half 90a on the palm side of the left wrist 90, and a block portion 11N that is formed integrally on one end portion (the right end portion in FIGS. 1 and 2(C)) 11f in the circumferential direction X1 of the first clamp portion 11M. The first clamp portion 11M is approximately formed into a plate shape having an approximately circular arc shape, obtained by cutting off a portion in a circumferential direction of a short cylinder. A slide hole 13 is formed in the block portion 11N so as to penetrate in a direction (referred to as "penetration direction") Y, which intersects with the circumferential direction X1. A cross section of the slide hole 13 taken orthogonally to the penetration direction Y is approximately rectangular (in particular, see FIG. 4(A)). As can be understood from FIGS. 1 and 2(C), a flat first pressing region 15 that is adjacent to the front of the slide hole 13, is inclined upward and to the right, and is for placing a finger, is formed on the upper side (outer circumferential surface 11a side) of the block portion 11N. "CLOSE" is displayed on the first pressing region 15. A flat fourth pressing region 18 that is adjacent to the back of the slide hole 13, is inclined upward and to the right, and is for placing a finger, is formed on the lower side (inner circumferential surface 11b side) of the block portion 11N. A pair of guide portions 11P and 11Q for guiding the slide bar 14 that will be described below are formed integrally directly below the block portion 11N so as to extend obliquely downward and to the right.

The lower-side member 12 includes a second clamp portion 12M that has a shape that is curved in a circumferential direction X2 along the half 90b on the back side of the left wrist 90, communication plate portions 12P and 12Q that are formed integrally on one end portion (right end portion in FIGS. 1 and 2(C)) 12f in the circumferential direction X2 of the second clamp portion 12M, a substrate portion 12S, the slide bar 14, and an end plate portion 12V. The second clamp portion 12M is approximately formed into a curved plate shape obtained by cutting off a portion in the circumferential direction of a short cylinder, similarly to the first clamp portion 11M. The dimension in the circumferential direction X2 of the second clamp portion 12M is set to be smaller than the dimension in the circumferential direction X1 of the first clamp portion 11M. The joining plate portions 12P and 12Q are formed into approximately flat shapes, and in order to increase their strength, their leading ends are merged and integrated. The substrate portion 12S has an approximately flat shape and is formed integrally on the united leading ends of the joining plate portion 12P on the upper side and the joining plate portion 12Q on the lower side so as to extend diagonally upward. A protrusion 12R is formed integrally on the substrate portion 12S so as to extend to the front side. A flat second pressing region 16 that is inclined upward and to the right and is for placing a finger is formed on the lower side (outer circumferential surface 12a side) of the protrusion 12R at a position corresponding to the first pressing region 15 of the upper-side member 11 in the front-rear (forward-back) direction. "CLOSE" is displayed on the protrusion 12R. The slide bar 14 extends upward and to the left from the substrate portion 12S, and more specifically, extends into the slide hole 13 of the first clamp portion 11M and fits therein. The shape of a cross section taken orthogonally to the direction in which the slide bar 14 extends is approximately rectangular and substantially matches the shape of the cross section of the slide hole 13. Accordingly, the slide bar 14 can slide with friction with respect to the slide hole 13. Note that chamfering is formed (in particular, see FIGS. 1 and 3) on corner portions 14c of the slide bar 14, and this prevents the corner portions 14c from catching on the slide hole 13. The end plate portion 12V is formed into a block shape having a dimension that is larger than the dimension of the cross section of the slide hole 13 in the front-rear direction and the left-right direction, and is attached to the leading end of the slide bar 14. A flat third pressing region 17 that is inclined upward to the right and is for placing a finger is formed on the upper side of the end plate portion 12V at a position corresponding to the fourth pressing region 18 of the upper-side member 11 in the front-rear direction. "OPEN" is displayed in the third pressing region 17.

The slide bar 14 can slide relatively from the leading end side (end plate portion 12V side) to the base side (substrate portion 12S side), or conversely, from the base side to the leading end side, with respect to the slide hole 13. When the slide hole 13 is located on the leading end side of the slide bar 14 and the gap between the first clamp portion 11M and the second clamp portion 12M is in the open state, the cuff 20 is said to be in the "open state". Conversely, when the slide hole 13 is located on the base side of the slide bar 14 and the gap between the first clamp portion 11M and the second clamp portion 12M is in the closed state, the cuff 20 is said to be in the "closed state".

In this example, when the cuff 20 is in the open state, the first pressing region 15 and the third pressing region 17 are located in substantially the same plane. This improves the appearance of the cuff 20.

As the lower side is approached from the upper side of the block portion 11N, the penetration direction Y of the slide hole 13 is inclined toward the outside (i.e., inclined toward the outside with respect to a vertical line (not shown) that extends in the vertical direction, and in this example, downward and to the right) in the circumferential direction X1 with respect to the right end portion 11f of the first clamp portion 11M. Furthermore, the slide hole 13 and the slide bar 14 are curved so as to protrude on the side near the other end portions (left end portions in FIGS. 1 and 2(C)) 11e and 12e of the first clamp portion 11M and the second clamp portion 12M.

In this example, the upper-side member 11 (includes the first clamp portion 11M, the block portion 11N, and the guide portions 11P and 11Q) is composed of ABS (acrylonitrile butadiene styrene copolymer) resin and is formed through integral molding. On the other hand, for the lower-side member 12, the second clamp portion 12M, the joining plate portions 12P and 12Q, the base portion 12S, and the slide bar 14 are formed through integral molding. The separately-produced end plate portion 12V is fixed by screws (not shown) to the leading end of the slide bar 14. The elements 12M, 12P, 12Q, 12S, 14, and 12V of the lower-side member 12 are also composed of ABS resin, similarly to the upper-side member 11.

In this example, the fluid bladder 22 that is to be inflated during blood pressure measurement is provided in approximately the entire region along the inner circumferential surface 11b of the first clamp portion 11M. Note that instead of or in addition to this, the fluid bladder may be provided along the inner circumferential surface 12b of the second clamp portion 12M.

Figure 5:
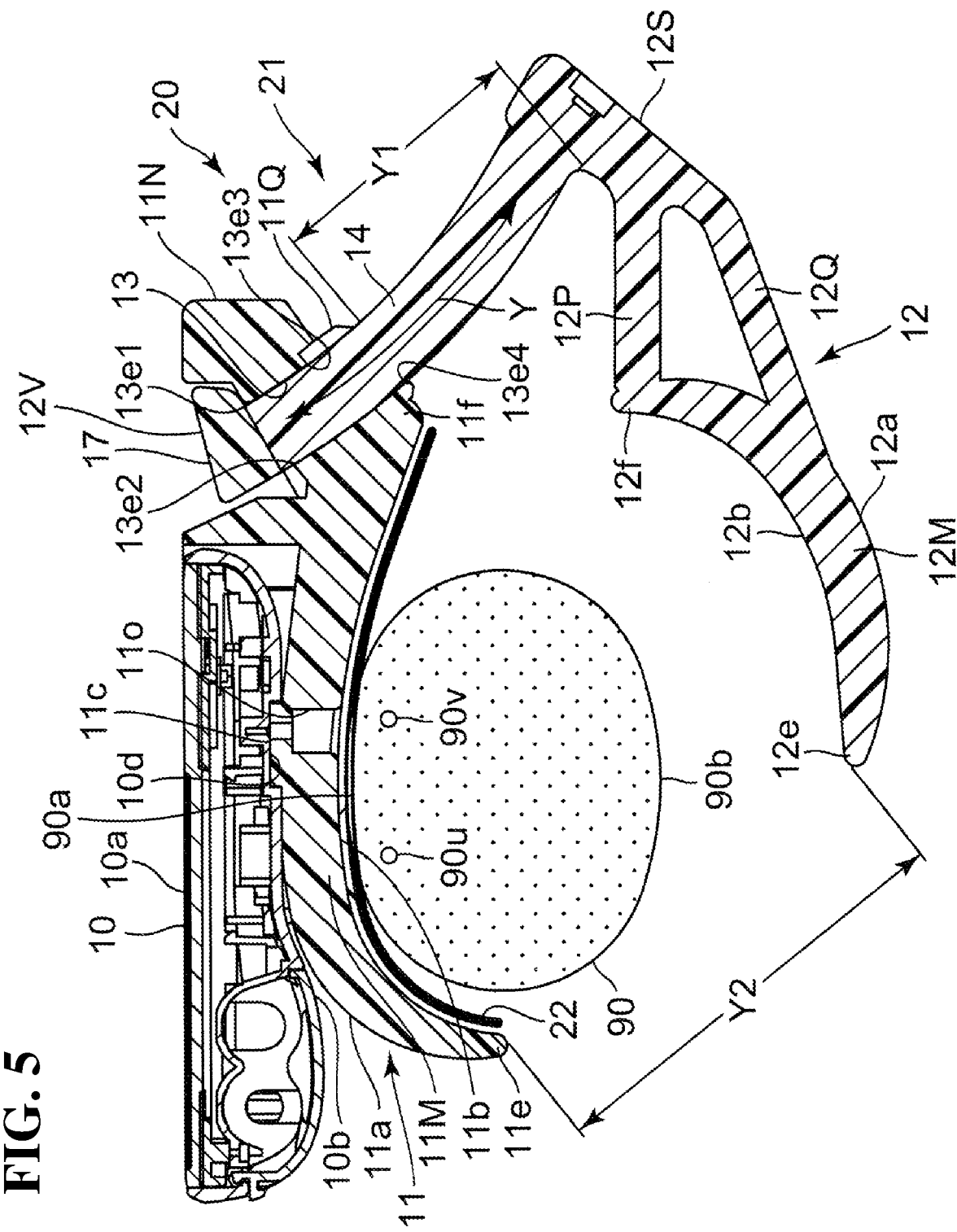
FIG. 5 is a diagram showing an operation of arranging the left wrist serving as the measurement site between the first clamp portion and the second clamp portion of the blood pressure measurement cuff.

FIG. 5 shows a cross section of the blood pressure monitor 1 that is parallel to that shown in FIG. 2(C). As shown in FIG. 5, among the edges constituting the exit/entrance on the side of the slide hole 13 located away from the second clamp portion 12M in the penetration direction Y, a second edge 13e2 on the side near the left end portion 11e of the first clamp portion 11M is at a position closer to the second clamp portion 12M in the penetration direction Y than the first edge 13e1 on the side away from the left end portion 11e of the first clamp portion 11M is. Also, among the edges that constitute the exit/entrance on the side of the slide hole 13 near the second clamp portion 12M in the penetration direction Y, the third edge 13e3 on the side away from the left end portion 11e of the first clamp portion 11M is at a position farther from the second clamp portion 12M in the penetration direction Y than the fourth edge 13e4 on the side near the left end portion 11e of the first clamp portion 11M is.

Curves are formed in the cross sections of the first edge 13e1 and the fourth edge 13e4 so as to reduce friction. On the other hand, the cross sections of the second edge 13e2 and the third edge 13e3 are formed into right angles or acute angles so as to increase friction.

As can be understood from FIG. 5, the main body 10 is attached integrally to the first clamp portion 11M of the upper-side member 11. Specifically, a recessed groove 10d is provided on the lower surface 10b of the main body 10. A protrusion 11c that fits into the groove 10d of the main body 10 is provided on the outer circumferential surface 11a of the first clamp portion 11M. The recessed groove 10d of the main body 10 is positioned by being fit on a protrusion 11c of the first clamp portion 11M, and is integrally attached using a fixing means (not shown) (e.g., a configuration in which a hook is provided on the first clamp portion 11M side and a locking hole that locks the hook is provided on the main body 10 side). A communication hole 11o that penetrates between the outer circumferential surface 11a side and the inner circumferential surface 11b side is provided at a site corresponding to the protrusion 11c. Air for inflating is supplied from a later-described pump arranged inside of the main body 10 to the fluid bladder 22 and air is discharged from the fluid bladder 22 through a pipe (not shown) that passes through the communication hole 11o.

As can be understood from FIGS. 1 and 3, an operation unit 52 with which a user (typically the measurement subject) of the blood pressure monitor 1 performs an operation is provided on the right end portion of the upper surface (outer surface) 10a of the main body 10, or in other words, in the region adjacent to the slide hole 13 of the first clamp portion 11M. In the operation portion 52, a measure/stop switch 52A with which the user instructs starting or stopping of measurement is arranged on the front side, or in other words, at a position corresponding to the second pressing region 16 in the front-rear (forward-back) direction, and a recording call switch 52B with which the user calls for measurement of the blood pressure is arranged on the back side. On the upper surface 10a of the main body 10, a display device (in this example, a liquid crystal display element) 50 for displaying blood pressure measurement results and information related to blood pressure is provided in a region outside of the operation unit 52.

The blood pressure monitor 1 is attached with the following operations (a) and (b) to the left wrist 90 serving as the measurement site. Note that at first, the gap between the first clamp portion 11M and the second clamp portion 12M is in the open state.

(a) First, as shown in FIG. 5, the measurement subject arranges the left wrist 90 between the first clamp portion 11M and the second clamp portion 12M.

At the time of the arranging operation (a), the measurement subject arranges the slide hole 13 and the slide bar 14 on a side near the center of the body of the measurement subject, and in this case, on a side near the right hand, in the periphery of the left wrist 90. Also, the half 90a on the palm side, through which the arteries 90u and 90v of the left wrist 90 pass, is oriented upward and brought into contact with the fluid bladder 22.

With the blood pressure monitor 1, as described above, the slide hole 13 and the slide bar 14 are curved so as to protrude on the side near the left end portions 11e and 12e of the first clamp portion 11M and the second clamp portion 12M. Accordingly, in the open state, in comparison to the case in which the slide hole 13 and the slide bar 14 are straight, a gap Y2 between the left end portion 11e of the first clamp portion 11M and the left end portion 12e of the second clamp portion 12e is more open (the distance Y2 is larger than the distance Y1 on the slide bar 14). As a result, the arranging operation (a) is easier.

Figure 6:
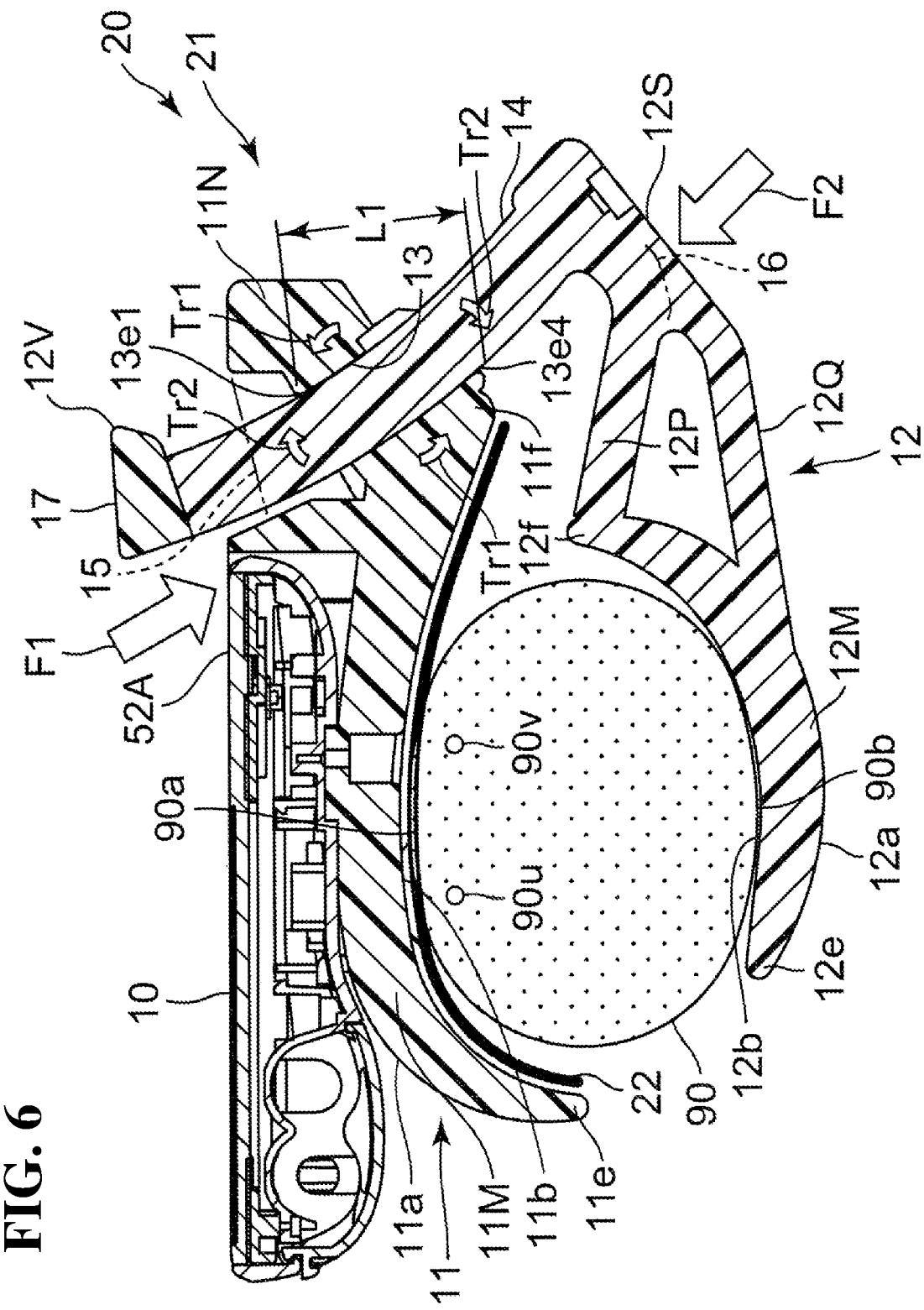
FIG. 6 is a diagram showing an operation of closing the blood pressure measurement cuff.

(b) Next, as shown in FIG. 6, the slide bar 14 is slid with respect to the slide hole 13 in the direction of closing the gap between the first clamp portion 11M and the second clamp portion 12M, whereby the left wrist 90 is sandwiched between the first clamp portion 11M and the second clamp portion 12M (the state in which the measurement site is sandwiched in this way is referred to as the "attached state").

At the time of the closing operation (b), the measurement subject can close the gap between the first clamp portion 11M and the second clamp portion 12M by applying forces F1 and F2 by pinching the first pressing region 15 and the second pressing region 16 with the thumb and another finger of the right hand so as to bring them close to each other. At this time, the first pressing region 15 is formed adjacent to the slide hole 13 and the second pressing region 16 is formed at a position corresponding to the first pressing region 15, and therefore the pressing force applied by the slide hole 13 to the slide bar 14 is relatively small, and the pressing force applied by the slide bar 14 to the slide hole 13 is relatively small. Specifically, regarding a moment Tr1 applied by the slide hole 13 to the slide bar 14 through the force F1, when the first pressing region 15 is used as a point of effort and the first edge 13e1 is used as a fulcrum, the fourth edge 13e4 corresponds to the point of action. Here, in comparison to the distance between the first pressing region 15 that is the point of effort and the first edge 13e1 that is the fulcrum (or more accurately, the length of the arm of the moment; the same applies hereinafter in this paragraph), the distance L1 between the first edge 13e1 that is the fulcrum and the fourth edge 13e4 that is the point of action is relatively long. Accordingly, the pressing force that acts on the fourth edge 13e4 (and the first edge 13e1) is relatively small. Also, regarding the moment Tr2 applied by the slide bar 14 to the slide hole 13 through the force F2, when the second pressing region 16 is used as a point of effort and the fourth edge 13e4 is used as a fulcrum, the first edge 13e1 corresponds to the point of action. Here, in comparison to the distance between the second pressing region 16 that is the point of effort and the fourth edge 13e4 that is the fulcrum, the distance L1 between the fourth edge 13e4 that is the fulcrum and the first edge 13e1 that is the point of action is relatively long. Accordingly, the pressing force that acts on the first edge 13e1 (and the fourth edge 13e4) is relatively small. Thus, the frictional force between the slide hole 13 and the slide bar 14 becomes relatively smaller. In addition, since curves are formed in the cross sections of the first edge 13e1 and the fourth edge 13e4, the frictional force between the slide hole 13 and the slide bar 14 decreases further. As a result, the measurement subject can easily close the gap between the first clamp portion 11M and the second clamp portion 12M. In other words, the closing operation (b) can be easily performed with one hand.

The blood pressure monitor 1 (cuff 20) is thus attached to the left wrist 90 using two operations, namely the arranging operation (a) and the closing operation (b). Accordingly, the blood pressure monitor 1 can be attached using a simpler operation compared to the conventional example (in which five operations are needed).

With the blood pressure monitor 1, in the attached state (e.g., FIG. 6) resulting from performing the arranging operation (a) and the closing operation (b) in sequence, the measurement subject performs the following measurement start instruction operation (c).

(c) The measure/stop switch 52A serving as the operation switch provided on the main body 10 is pressed to input a blood pressure measurement start instruction to the main body 10. Accordingly, the fluid bladder 22 provided along the inner circumferential surface 11b of the first clamp portion 11M is inflated, and blood pressure measurement is performed (the flow of blood pressure measurement will be described later).

Figure 7:
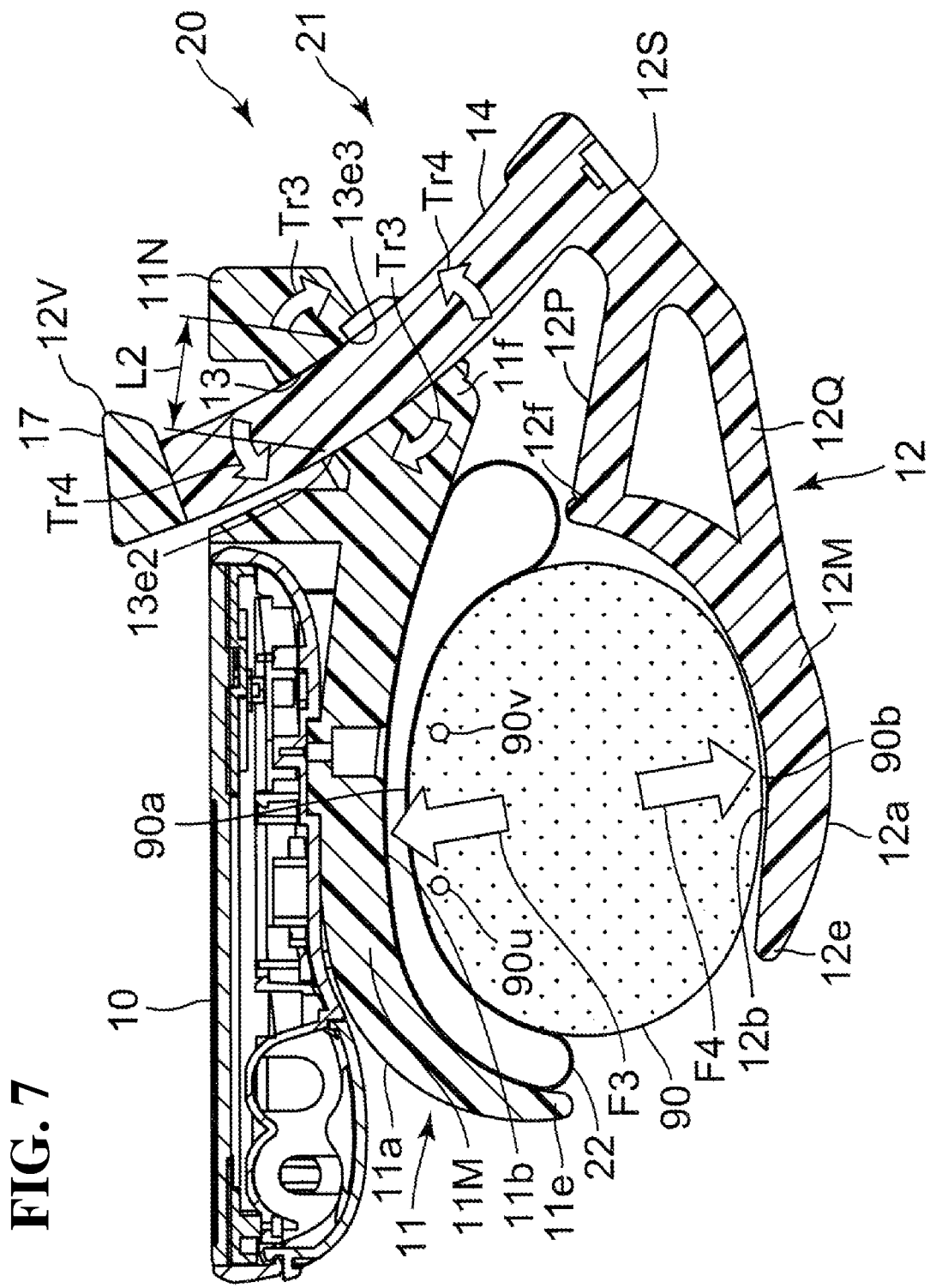
FIG. 7 is a diagram showing forces applied to the blood pressure measurement cuff during blood pressure measurement.

During the blood pressure measurement, as shown in FIG. 7, the fluid bladder 22 provided along the inner circumferential surface 11b of the first clamp portion 11M is inflated and forces F3 and F4 in the direction of relatively opening are applied in the gap between the inner circumferential surface 11b of the first clamp portion 11M and the inner circumferential surface 12b of the second clamp portion 12M. However, the pressing force increases due to a moment being applied to the slide bar 14 from the slide hole 13, and the pressing force increases due to a moment being applied from the slide bar 14 to the slide hole 13. Specifically, regarding a moment Tr3 applied by the slide hole 13 to the slide bar 14 through the force F3, when the inner circumferential surface 11b of the first clamp portion 11M is used as the point of effort and the second edge 13e2 of the slide hole 13 is used as the fulcrum, the third edge 13e3 of the slide hole 13 corresponds to the point of action. Here, in comparison to the distance (or more accurately, the length of the arm of the moment; the same applies hereinafter in the paragraph) between the inner circumferential surface 11*b* of the first clamp portion 11M that is the point of effort and the second edge 13*e*2 that is the fulcrum, the distance L2 between the second edge 13*e*2 that is the fulcrum and the third edge 13*e*3 that is the point of action is relatively short. Accordingly, the pressing force that acts on the third edge 13*e*3 (and the second edge 13*e*2) increases. Also, regarding a moment Tr4 applied by the slide bar 14 to the slide hole 13 through the force F4, when the inner circumferential surface 12*b* of the second clamp portion 12M is used as the point of effort and the third edge 13*e*3 of the slide hole 13 is used as the fulcrum, the second edge 13*e*2 of the slide hole 13 corresponds to the point of action. Here, in comparison to the distance between the inner circumferential surface 12*b* of the second clamp portion 12M that is the point of effort and the third edge 13*e*3 that is the fulcrum, the distance L2 between the third edge 13*e*3 that is the fulcrum and the second edge 13*e*2 that is the point of action is relatively short. Accordingly, the pressing force that acts on the second edge 13*e*2 (and the third edge 13*e*3) increases. In particular, as described above, the second edge 13*e*2 is at a position closer to the second clamp portion 12M in the penetration direction Y than the first edge 13*e*1 is, and the third edge 13*e*3 is at a position farther from the second clamp portion 12M in the penetration direction Y than the fourth edge 13*e*4 is. In other words, the distance L2 between the second edge 13*e*2 and the third edge 13*e*3 is set to be shorter than the distance L1 between the first edge 13*e*1 and the fourth edge 13*e*4. Accordingly, the pressing force that acts on the second edge 13*e*2 and the third edge 13*e*3 further increases. Thus, the frictional force that acts between the slide hole 13 and the slide bar 14 increases. In addition, since the cross sections of the second edge 13*e*2 and the third edge 13*e*3 are formed into right angles or acute angles, the frictional force between the slide hole 13 and the slide bar 14 further increases. As a result, the first clamp portion 11M is not likely to open with respect to the second clamp portion 12M (and the left wrist 90), and the attached state is reliably maintained.

After the blood pressure measurement, the blood pressure monitor 1 is removed with the following operations (d) and (e).

Figure 8:
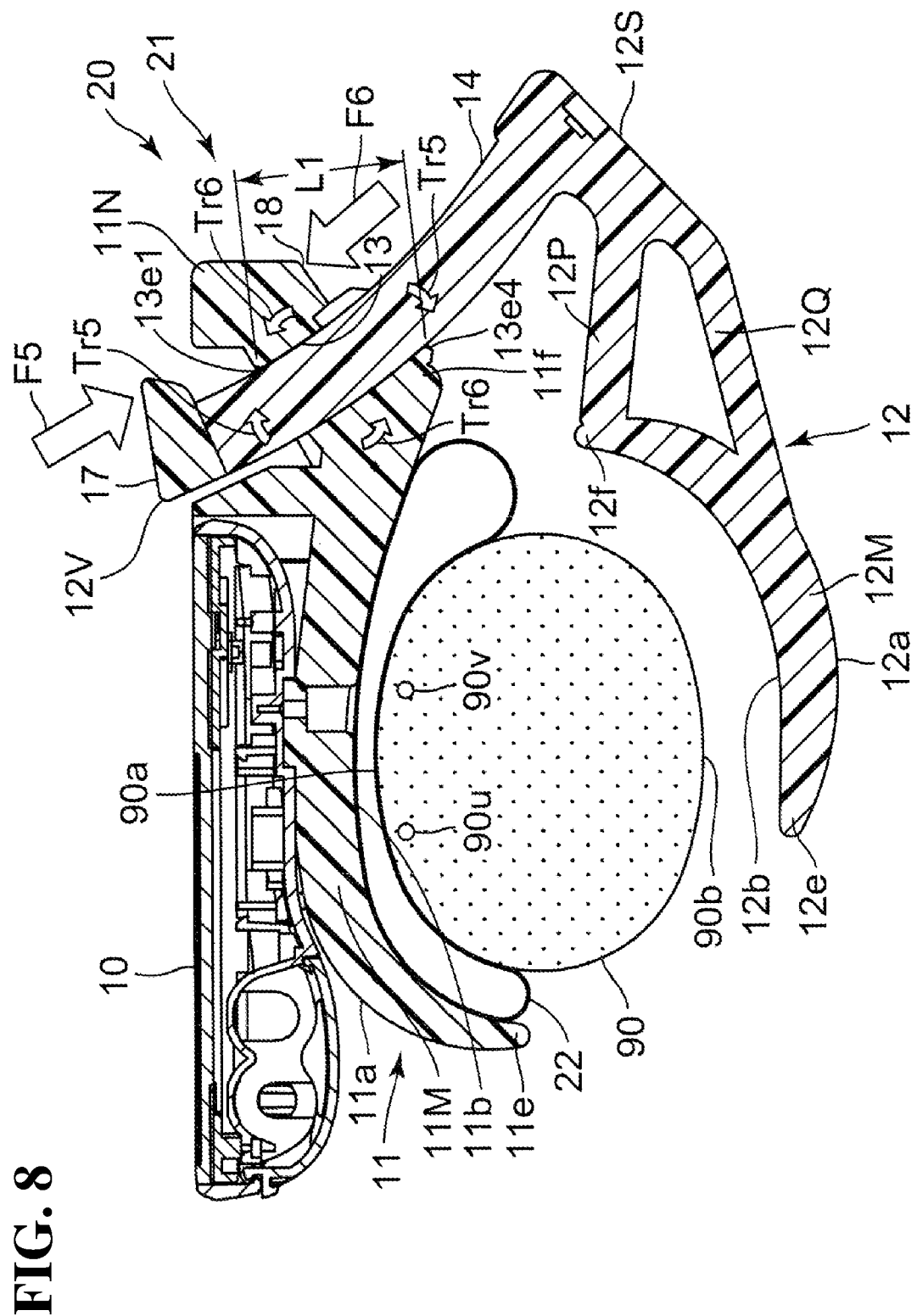
FIG. 8 is a diagram showing an operation of opening the blood pressure measurement cuff.

(d) After measurement ends, as shown in FIG. 8, the measurement subject slides the slide bar 14 with respect to the slide hole 13 in the direction of opening the gap between the first clamp portion 11M and the second clamp portion 12M, whereby the gap between the first clamp portion 11M and the second clamp portion 12M is set to the open state.

At the time of the opening operation (d), the measurement subject can open the gap between the first clamp portion 11M and the second clamp portion 12M by applying forces F5 and F6 by pinching the third pressing region 17 and the fourth pressing region 18 with the thumb and another finger of the right hand so as to bring them close to each other. At this time, the third pressing region 17 is formed on the leading end of the slide bar 14 and the fourth pressing region 18 is formed adjacent to the slide hole 13, and therefore the pressing force applied by the slide bar 14 to the slide hole 13 is relatively small and the pressing force applied by the slide hole 13 to the slide bar 14 is relatively small. Specifically, regarding a moment Tr5 applied by the slide bar 14 to the slide hole 13 through the force F5, when the third pressing region 17 is used as a point of effort and the first edge 13*e*1 is used as a fulcrum, the fourth edge 13*e*4 corresponds to the point of action. Here, in comparison to the distance between the third pressing region 17 that is the point of effort and the first edge 13*e*1 that is the fulcrum, the distance L1 between the first edge 13*e*1 that is the fulcrum and the fourth edge 13*e*4 that is the point of action is relatively long. Accordingly, the pressing force that acts on the fourth edge 13*e*4 (and the first edge 13*e*1) is relatively smaller. Also, regarding a moment Tr6 applied by the slide hole 13 to the slide bar 14 through the force F6, when the fourth pressing region 18 is used as a point of effort and the first edge 13*e*1 is used as a fulcrum, the fourth edge 13*e*4 corresponds to the point of action. Here, in comparison to the distance between the fourth pressing region 18 that is the point of effort and the first edge 13*e*1 that is the fulcrum (or more accurately, the length of the arm of the moment; the same applies hereinafter in this paragraph), the distance L1 between the first edge 13*e*1 that is the fulcrum and the fourth edge 13*e*4 that is the point of action is relatively long. Accordingly, the pressing force that acts on the fourth edge 13*e*4 (and the first edge 13*e*1) is relatively smaller. Thus, the frictional force between the slide hole 13 and the slide bar 14 is relatively smaller. In addition, since curves are formed in the cross sections of the first edge 13*e*1 and the fourth edge 13*e*4, the frictional force between the slide hole 13 and the slide bar 14 decreases further. As a result, the measurement subject can easily open the gap between the first clamp portion 11M and the second clamp portion 12M. In other words, the opening operation (d) can be performed easily with one hand.

(e) Next, the measurement subject removes the left wrist 90 from the gap between the first clamp portion 11M and the second clamp portion 12M.

Thus, according to this blood pressure monitor 1, blood pressure measurement can be performed with a simple operation.

With the blood pressure monitor 1, at the time of the closing operation (b) and the opening operation (d), the first clamp portion 11M and the second clamp portion 12M move (slide) along the plane including the curved slide bar 14. In other words, the slide bar 14, which has a rectangular cross section, fits into the slide hole 13, which has a rectangular cross section, and therefore the first clamp portion 11M is restricted from rotating about the slide bar 14. Accordingly, even if the operations (a) to (e) are repeated, after the closing operation (b), the first clamp portion 11M and the second clamp portion 12M will always enter a state of opposing each other in the vertical direction and being able to compress the left wrist 90.

Also, with the blood pressure monitor 1, as shown in FIG. 1, the measure/stop switch 52A serving as the operation switch is provided at a position corresponding to the second pressing region 16 in the front-rear (forward-back) direction in a region of the outer surface of the main body 10 that is adjacent to the slide hole 13 of the first clamp portion 11M. Accordingly, the measurement subject can easily close the gap between the first clamp portion 11M and the second clamp portion 12M by pinching the measure/stop switch 52A and the second pressing region 16 with the thumb and another finger of the right hand so as to bring them close to each other. In other words, the closing operation (b) can be easily performed with one hand. Also, by performing the closing operation (b), it is possible to perform the measurement start instruction operation (c), or in other words, an operation of inputting an instruction to start blood pressure measurement to the main body 10 by pressing the measure/stop switch 52A. In other words, the measurement subject can simultaneously perform the closing operation (b) and the measurement start instruction operation (c), and thus can perform blood pressure measurement with a simpler operation.

Note that since there is friction between the slide hole 13 and the slide bar 14, it is easy to retain the blood pressure monitor 1 in a state (open state) in which the gap between the first clamp portion 11M and the second clamp portion 12M is open. However, the cuff 20 may be retained in a state (closed state) in which the gap between the first clamp portion 11M and the second clamp portion 12M is closed. In this case, during use of the blood pressure monitor 1, an operation of opening the gap between the first clamp portion 11M and the second clamp portion 12M is added before the arranging operation (a).

Figure 9:
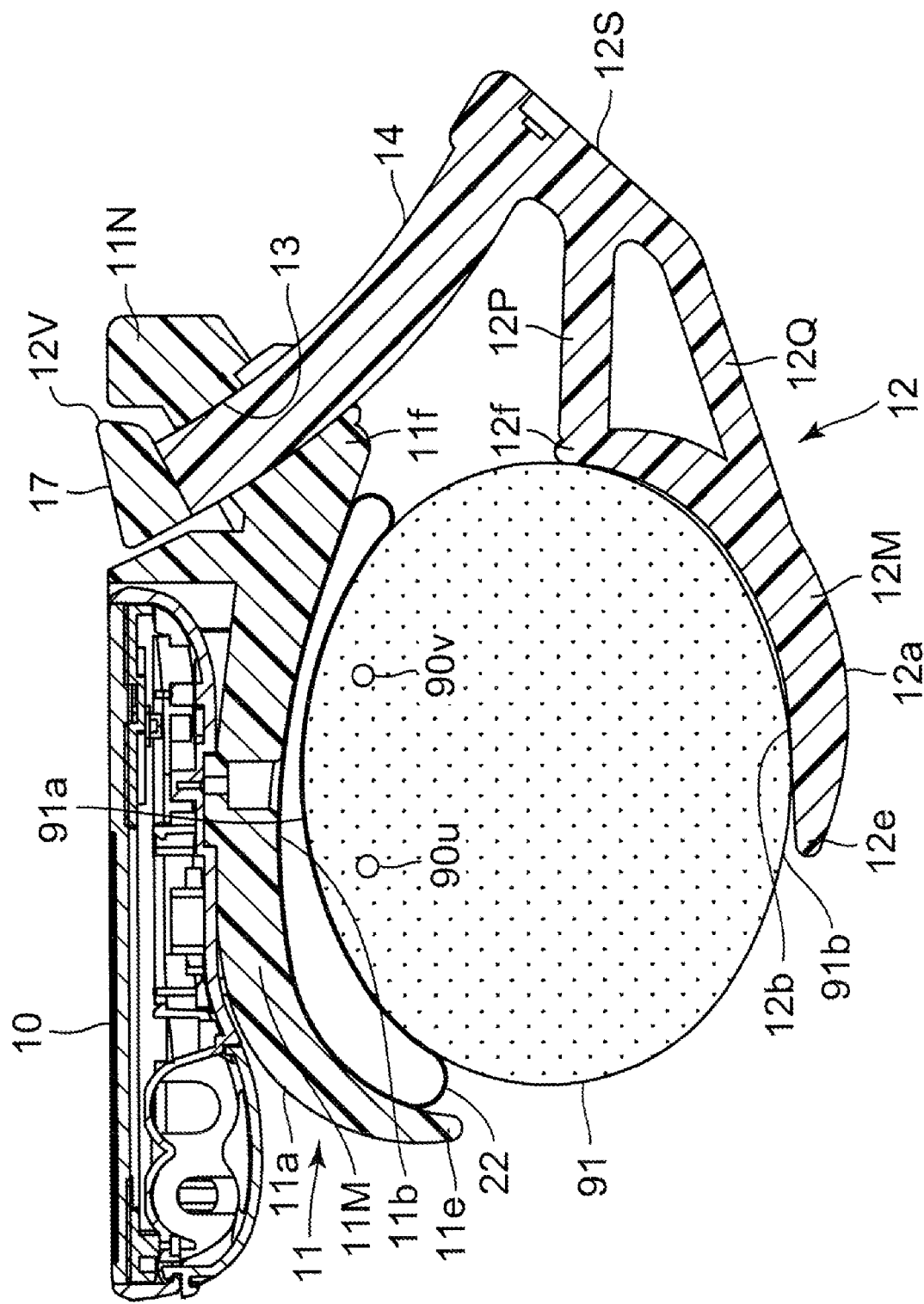
FIG. 9 is a diagram showing a state in which a blood pressure monitor including the blood pressure measurement cuff is attached to a thick left wrist serving as the measurement site.

FIG. 9 shows a state in which the blood pressure monitor 1 is attached to a left wrist 91, which is thicker than the left wrist 90. As can be understood from FIG. 9, the dimension in the circumferential direction of the first clamp portion 11M is set to be a dimension that completely covers the half 91a on the palm side of the thick left wrist 91. The fluid bladder 22 provided in approximately the entire region along the inner circumferential surface 11b of the first clamp portion 11M covers a large portion of the half 91a on the palm side of the thick left wrist 91. Accordingly, due to the fluid bladder 22 being inflated, the arteries 90u and 90v are compressed, and blood pressure measurement is performed smoothly. Note that in this example, due to the fact that the dimension in the circumferential direction of the second clamp portion 12M is smaller than the dimension in the circumferential direction of the first clamp portion 11M, the lower-left portion of the thick left wrist 91 that is far from the slide bar 14 protrudes outward with respect to the left end portion 12e of the second clamp portion 12M. However, since the arteries 90u and 90v that are to be compressed exist in the half 91a on the palm side and do not exist in the half 91b on the back side, blood pressure measurement is not hampered.

Figure 10:
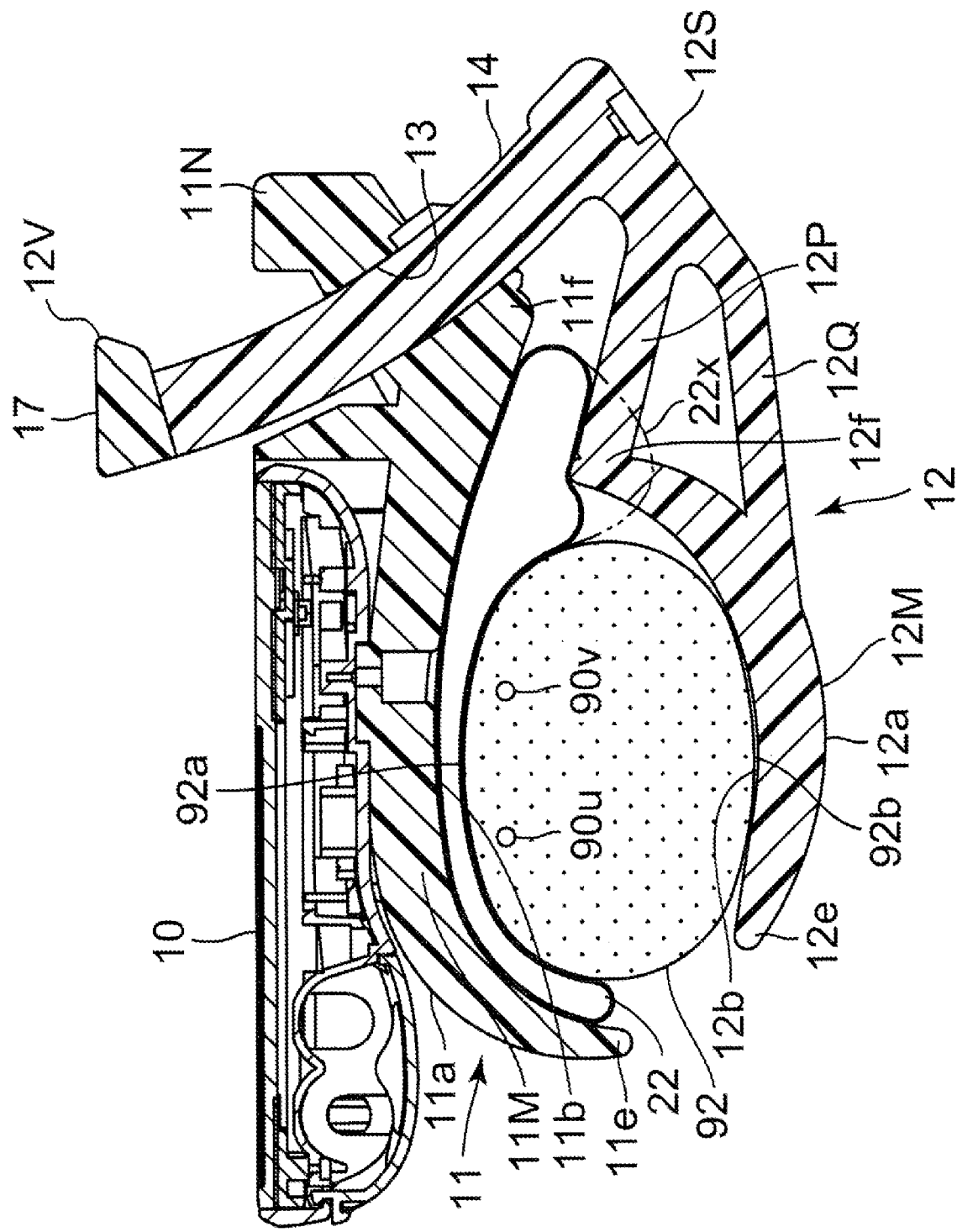
FIG. 10 is a diagram showing a state in which the blood pressure monitor including the blood pressure measurement cuff is attached to the narrow left wrist serving as the measurement site.

FIG. 10 shows a state in which the blood pressure monitor 1 is attached to a left wrist 92 that is thinner than the above-described left wrist 90. In the case of the thin left wrist 92, at the time of the closing operation (b), as the second clamp portion 12M relatively approaches the first clamp portion 11M, the second clamp portion 12M significantly moves diagonally approximately upward and to the left while the opposing region is changed toward the left end portion 11e from the right end portion 11f of the first clamp portion 11M (rotation of the orientation accompanying the curving of the slide hole 13 and the slide bar 14 is also included). Also, the second clamp portion 12M enters a state of conforming to the half 92d on the back side of the thin left wrist 92. Accordingly, the thin left wrist 92 can be reliably sandwiched between the first clamp portion 11M and the second clamp portion 12M.

In this attached state, as can be understood from FIG. 10, the half 92a on the palm side of the thin left wrist 92 is held at a position biased to the left end portion 11e in the circumferential direction with respect to the first clamp portion 11M. As a result, the right end portion 22x of the fluid bladder 22 enters a state of not being in contact with the left wrist 92 (in particular, the half 92a on the palm side). For this reason, unless there is some kind of contrivance, when the fluid bladder 22 is inflated, the right end portion 22x of the fluid bladder 22 will swell significantly toward the second clamp portion 12M as indicated by the two-dot chain line in FIG. 10, and there is a possibility that blood pressure measurement will be hindered. Here, with the blood pressure monitor 1, as the gap between the first clamp portion 11M and the second clamp portion approaches the closed state, the right end portion 12f of the second clamp portion 12M and the communication plate portion 12P adjacent thereto approach the right end portion 11f of the first clamp portion 11M (i.e., the right end portion 22x of the fluid bladder 22). As a result, in the state of being attached to the thin left wrist 92, the elements 12f and 12P restrict swelling of the opposing portion (right end portion) 22x of the fluid bladder 22. Accordingly, blood pressure measurement is performed accurately and smoothly.

Thus, the blood pressure monitor 1 can smoothly perform blood pressure measurement on any size of wrist ranging from that of a thick left wrist 91 to that of a thin left wrist 92 due to the second clamp portion 12M moving downward to the left or upward to the left relative to the first clamp portion 11M.

With the above-described operation procedure, it was assumed that the blood pressure monitor 1 is attached to a measurement site belonging to the left half of the body (e.g., the left wrist), but there is no limitation to this. The blood pressure monitor 1 may be attached to a measurement site belonging to the right half of the body (e.g., the right wrist). In this case, the slide hole 13 and the slide bar 14 are arranged on the side near the center of the body of the measurement subject, and in this case, on the side near the left hand, in the periphery of the measurement site. In this case, the measurement subject can easily close the gap between the first clamp portion 11M and the second clamp portion 12M by pinching the first pressing region 15 and the second pressing region 16 with the thumb and another finger of the left hand. Also, the measurement subject can easily open the gap between the first clamp portion 11M and the second clamp portion 12M by pinching the third pressing region 17 and the fourth pressing region 18 with the thumb and another finger of the left hand. In other words, the operations can be easily performed with the left hand (one hand).

Figure 14:
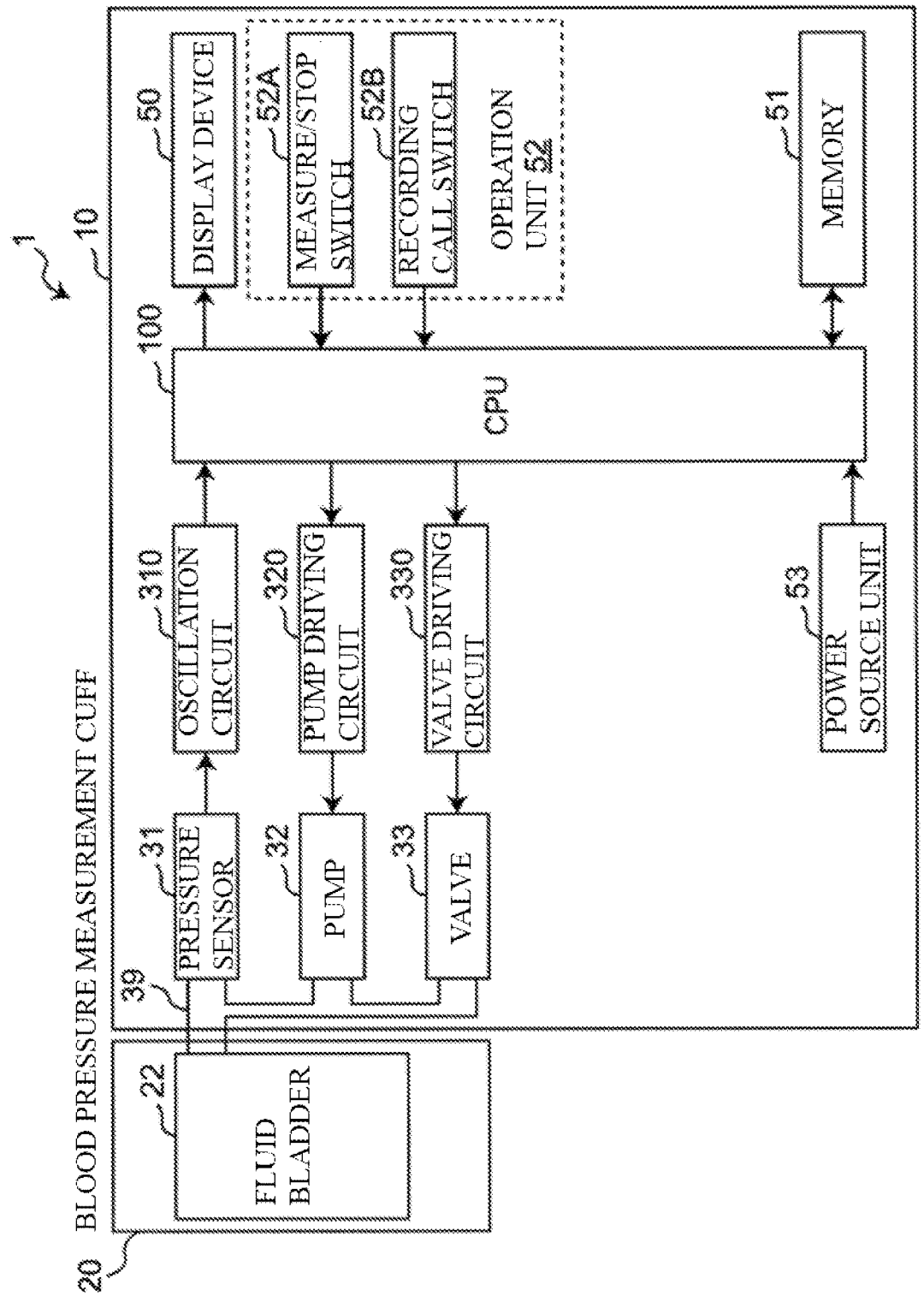
FIG. 14 is a diagram showing a block configuration of the blood pressure monitor.

FIG. 14 shows a schematic block configuration of the blood pressure monitor 1. As elements for blood pressure measurement, a CPU (Central Processing Unit) 100 serving as a control unit, a memory 51 serving as a storage unit, a power source unit 53, a pump 32, a valve 33, and a pressure sensor 31 are included along with the above-described display device 50 and operation unit 52 in the main body 10 of the blood pressure monitor 1. Also, an oscillation circuit 310 that converts the output from the pressure sensor 31 into a frequency, a pump driving circuit 320 that drives the pump 32, and a valve driving circuit 330 that drives the valve 33 are built into the main body 10.

The display device 50 includes a display, an indicator, and the like, and displays predetermined information in accordance with a control signal from the CPU 100.

The measure/stop switch 52A and the recording call switch 52B that are included in the operation unit 52 input operation signals corresponding to instructions performed by the user to the CPU 100.

The memory 51 stores data of programs for controlling the blood pressure monitor 1, data to be used to control the blood pressure monitor 1, setting data for setting various functions of the blood pressure monitor 1, data of blood pressure value measurement results, and the like. Also, the memory 51 is used as a work memory and the like for when a program is executed.

In accordance with the program for controlling the blood pressure monitor 1 that is stored in the memory 51, the CPU 100 performs control for driving the pump 32 and the valve 33 in response to an operation signal from the operation unit 52. Also, based on the signal from the pressure sensor 31, the CPU 100 calculates the blood pressure value and controls the display device 50 and the memory 51.

The power source unit 53 supplies power to the units, namely the CPU 100, the pressure sensor 31, the pump 32, the valve 33, the display device 50, the memory 51, the oscillation circuit 310, the pump driving circuit 320, and the valve driving circuit 330.

The pump 32 supplies air to the fluid bladder 22 contained in the cuff 20 in order to increase the pressure (cuff pressure) in the fluid bladder 22. The valve 33 is opened and closed in order to discharge or seal the air in the fluid bladder 22 and control the cuff pressure. The pump driving circuit 320 drives the pump 32 based on the control signal supplied from the CPU 100. The valve driving circuit 330 opens and closes the valve 33 based on the control signal applied from the CPU 100.

The pressure sensor 31 and the oscillation circuit 310 function as a pressure detection unit that detects the pressure of the cuff. For example, the pressure sensor 31 is a piezoresistance pressure sensor, and is connected to the fluid bladder 22 contained in the pump 32, the valve 33, and the cuff 20 via a cuff air tube 39. In this example, the oscillation circuit 310 oscillates based on an electrical signal value obtained based on a change in electrical resistance caused by a piezoresistant effect from the pressure sensor 31, and outputs a frequency signal having a frequency corresponding to the electrical signal value of the pressure sensor 31 to the CPU 100.

In the case of measuring the blood pressure in accordance with a general oscillometric method, the following operation is approximately performed. That is, the cuff is attached in advance to the measurement site (arm, etc.) of the measurement subject, and during measurement, the pump and valve are controlled so as to increase the cuff pressure to be higher than the systolic blood pressure, whereafter the cuff pressure is gradually decreased. In the process of reducing the pressure, the cuff pressure is detected by the pressure sensor, and variation in the arterial capacity that occurs in the arteries at the measurement site is obtained as a pulse signal. Based on the changes (mainly the rising edges and falling edges) in the amplitude of the pulse signal accompanying changes in the cuff pressure at that time, the systolic blood pressure and the diastolic blood pressure are calculated.

Figure 15:
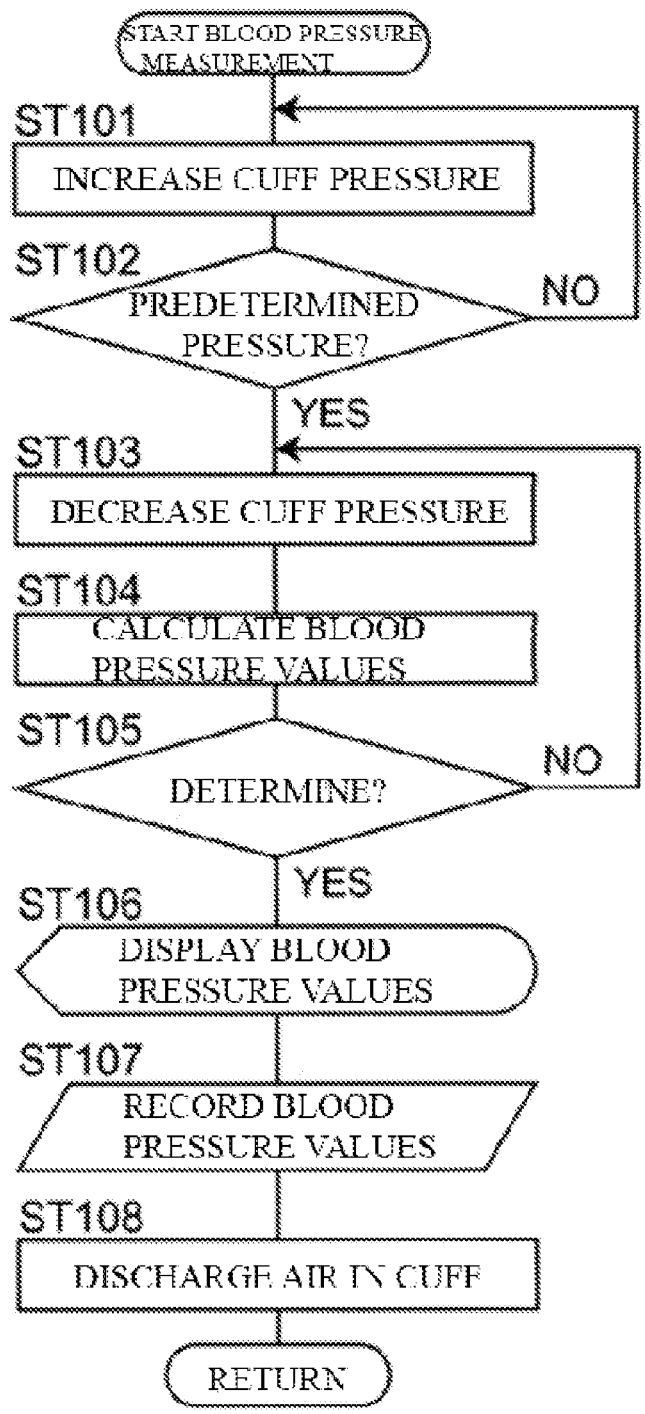
FIG. 15 is a diagram showing a flow of blood pressure measurement performed by the blood pressure monitor.

With the blood pressure monitor 1, the blood pressure values of the measurement subject are measured by the CPU 100 using an oscillometric method in accordance with the flow shown in FIG. 15.

Specifically, when the measure/stop switch 52A is pressed, as shown in FIG. 15, the blood pressure monitor 1 starts blood pressure measurement. At the start of blood pressure measurement, the CPU 100 initializes the processing memory region and outputs a control signal to the valve driving circuit 330. Based on the control signal, the valve driving circuit 330 releases the valve 33 to discharge the air in the fluid bladder 22 of the cuff 20. Next, control for adjusting the output sensor 31 to 0 mmHg is performed.

When blood pressure measurement is started, first, the CPU 100 closes the valve 33 via the valve driving circuit 330 and thereafter performs control for driving the pump 32 via the pump driving circuit 320 and sending air to the fluid bladder 22. Accordingly, the fluid bladder 22 is inflated and the cuff pressure gradually increases (step ST101).

When the cuff pressure is increased and reaches a predetermined pressure (YES in step ST102), the CPU 100 performs control for stopping the pump 32 via the pump driving circuit 320 and thereafter gradually releasing the valve 33 via the valve driving circuit 330. Accordingly, the fluid bladder 22 is contracted and the cuff pressure gradually decreases (step ST103).

Here, the predetermined pressure is a pressure that is sufficiently higher than the systolic blood pressure of the measurement subject (e.g., systolic blood pressure+30 mmHg), and the predetermined pressure is stored in the memory 51 in advance or the CPU 100 determines the predetermined pressure by estimating the systolic blood pressure using a predetermined calculation method while the cuff pressure is increased (e.g., see JP 2001-70263A).

Also, for the pressure decrease speed, a target pressure decrease speed that is a target is set during inflation of the cuff, and the CPU 100 controls the opening degree of the valve 33 so as to reach the target pressure decrease speed (see JP 2001-70263A).

In the pressure decrease process, the pressure sensor 31 detects the cuff pressure signal (indicated by reference numeral Pc) indicating the pressure of the cuff 20 via the cuff 20. Based on the cuff pressure signal Pc, the CPU 100 calculates the blood pressure values (systolic blood pressure and diastolic blood pressure) by applying a known algorithm through the oscillometric method (step ST104). Note that the calculation of the blood pressure values is not limited to being performed in the pressure decrease process, and may be performed in the pressure increase process.

Upon determining the blood pressure value by calculation (YES in step ST105), the CPU 100 performs control for displaying the calculated blood pressure values on the display device 50 (step ST106) and storing the blood pressure values in the memory 51 (step ST107).

Next, when the measure/stop switch 52A is pressed again, the CPU 100 performs control for releasing the valve 33 via the valve driving circuit 330 and discharging the air in the fluid bladder 22 of the cuff 20 (step ST108). Accordingly, the blood pressure measurement is stopped.

Modified Example

Figure 11:
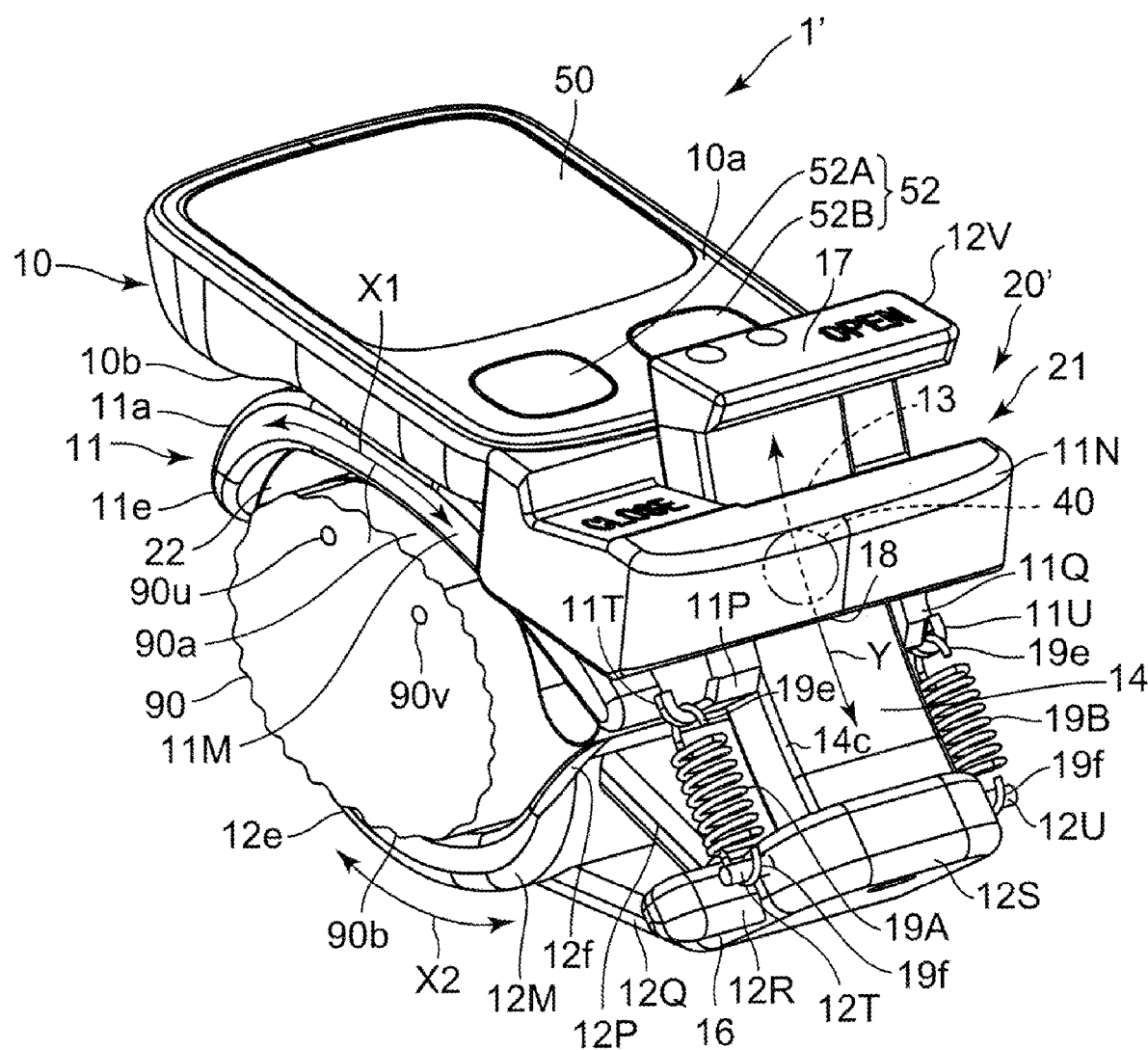
FIG. 11 is a perspective view showing the exterior of the blood pressure monitor including a blood pressure measurement cuff according to a modified example.

FIG. 11 shows the exterior of a blood pressure monitor 1' that includes a cuff (indicated by reference numeral 20') according to a modified example of the above-described cuff 20. Note that in FIG. 11 (and later-described FIGS. 12 and 13), constituent elements that are the same as those in FIGS. 1 to 10 are denoted by the same reference numerals.

With the blood pressure monitor 1', coil springs 19A and 19B serving as elastic members are provided between the upper-side member 11 and the lower-side member 12. Specifically, C-shaped hooks 11T and 11U are formed integrally on guide portions 11P and 11Q (formed adjacent to the slide hole 13) provided on the block portion 11N of the upper-side member 11. On the other hand, locking bars 12T and 12U that extend in the front-rear direction are formed integrally on the substrate portion 12S of the lower-side member 12. The hooks 11T and 11U and the locking bars 12T and 12U are at positions that correspond to each other in the front-rear direction. Both of the coil springs 19A and 19B have the C-shaped hooks 19e and 19f on both ends thereof. The coil spring 19A spans between the hook 11T and the locking bar 12T via the hooks 19e and 19f. Also, the coil spring 19B spans between the hook 11U and the locking bar 12U via the hooks 19e and 19f. The coil springs 19A and 19B apply tensile forces between the block portion 11N of the upper-side member 11 and the substrate portion 12S of the lower-side member 12 in a direction of bringing the first clamp portion 11M and the second clamp portion 12M close to each other. In this example, the tensile forces of the coil springs 19A and 19B when the gap between the first clamp portion 11M and the second clamp portion 12M is in the open state are set to be sufficiently greater than the frictional force between the slide hole 13 and the slide bar 14.

Also, in this example, a known push-push (also referred to as "push-lock push-open") latch mechanism 40 including a heart-shaped cam (not shown) is provided inside of the block portion 11N. When the block portion 11N and the end plate portion 12V of the slide bar 14 are brought close to each other due to an external force that acts against the tensile forces of the coil springs 19A and 19B, the latch mechanism 40 is engaged in a state in which the block portion 11N and the end plate portion 12V are slightly separated from each other, and then, when the block portion 11N and the end plate portion 12V of the slide bar 14 are brought close to each other again due to the external force, the engagement between the block portion 11N and the end plate portion 12V is canceled.

Other configurations of the blood pressure monitor 1' are similar to the configurations of the blood pressure monitor 1.

The blood pressure monitor 1 is attached with the following operations (f) to (h) to the left wrist 90 serving as the measurement site. Note that at first, the gap between the first clamp portion 11M and the second clamp portion 12M is in the closed state.

(f) First, as shown in FIG. 12(A) (and FIG. 12(B), which shows a view from the right side), the measurement subject slides the slide bar 14 with respect to the slide hole 13 in the direction of opening the gap between the first clamp portion 11M and the second clamp portion 12M so as to set the gap between the first clamp portion 11M and the second clamp portion 12M to the open state.

At the time of the opening operation (f), the measurement subject can open the gap between the first clamp portion 11M and the second clamp portion 12M by applying forces F7 and F8 against the tensile forces F9 and F10 of the coil springs 19A and 19B by pinching the third pressing region 17 and the fourth pressing region 18 with the thumb and another finger of the right hand so as to bring them close to each other. At this time, the third pressing region 17 is formed on the leading end of the slide bar 14 and the fourth pressing region 18 is formed adjacent to the slide hole 13, and therefore the pressing force applied by the slide bar 14 to the slide hole 13 is relatively small and the pressing force applied by the slide hole 13 to the slide bar 14 is relatively small, similarly to the description above regarding the opening operation (d). Thus, the frictional force between the slide hole 13 and the slide bar 14 is relatively smaller. In addition, since curves are formed in the cross sections of the first edge 13e1 and the fourth edge 13e4, the frictional force between the slide hole 13 and the slide bar 14 decreases further. As a result, the measurement subject can easily open the gap between the first clamp portion 11M and the second clamp portion 12M. In other words, the opening operation (f) can be performed easily with one hand.

When the measurement subject performs the opening operation (f), in this example, the latch mechanism 40 engages in a state in which the block portion 11N and the end plate portion 12V are slightly separated from each other. Accordingly, the open state of the gap between the first clamp portion 11M and the second clamp portion 12M is maintained.

(g) While the open state is maintained, as shown in FIGS. 12(A) and 12(B), the measurement subject arranges the left wrist 90 between the first clamp portion 11M and the second clamp portion 12M.

At the time of the arranging operation (g), the measurement subject arranges the slide hole 13 and the slide bar 14 on a side near the center of the body of the measurement subject, and in this case, on a side near the right hand, in the periphery of the left wrist 90. Also, the half 90a on the palm side, through which the arteries 90u and 90v of the left wrist 90 pass, is oriented upward and brought into contact with the fluid bladder 22.

With the blood pressure monitor 1', similarly to the above-described blood pressure monitor 1, the slide hole 13 and the slide bar 14 are curved so as to protrude on the side near the left end portions 11e and 12e of the first clamp portion 11M and the second clamp portion 12M. Accordingly, in the open state, in comparison to the case in which the slide hole 13 and the slide bar 14 are straight, a gap between the left end portion 11e of the first clamp portion 11M and the left end portion 12e of the second clamp portion 12M is more open. As a result, the arranging operation (g) is easier.

(h) Next, the measurement subject applies forces F7 and F8 against the tensile forces F9 and F10 of the coil springs 19A and 19B by pinching the third pressing region 17 and the fourth pressing region 18 with the thumb and another finger of the right hand again so as to bring them close to each other. Upon doing so, as shown in FIG. 13(A) (and FIG. 13(B), which shows a view from the right side), the latch mechanism 40 cancels the engagement between the block portion 11N and the end plate portion 12V. Accordingly, due to the tensile forces F9 and F10 (set to be sufficiently greater than the frictional force between the slide hole 13 and the slide bar 14) of the coil springs 19A and 19B, the slide bar 14 slides with respect to the slide hole 13 in the direction of closing the gap between the first clamp portion 11M and the second clamp portion 12M, the left wrist 90 is sandwiched between the first clamp portion 11M and the second clamp portion 12M, and the attached state is entered.

Here, since the hooks 11T and 11U to which the coil springs 19A and 19B apply the tensile forces are formed adjacent to the slide hole 13 and the locking bars 12T and 12U are formed at positions corresponding to the hooks 11T and 11U, the pressing force applied by the slide hole 13 to the slide bar 14 is relatively small, and the pressing force applied by the slide bar 14 to the slide hole 13 is relatively small. Thus, the frictional force between the slide hole 13 and the slide bar 14 is relatively smaller. In addition, since curves are formed in the cross sections of the first edge 13e1 and the fourth edge 13e4, the frictional force between the slide hole 13 and the slide bar 14 decreases further. As a result, the gap between the first clamp portion 11M and the second clamp portion 12M is easily closed. The measurement subject does not need to apply an external force to close the gap between the first clamp portion 11M and the second clamp portion 12M.

The blood pressure monitor 1' (cuff 20') is attached to the left wrist 90 with the three above-described operations (f) to (h). Accordingly, the blood pressure monitor 1' can be attached using a simpler operation compared to the conventional example (requiring five operations).

Figure 13B:
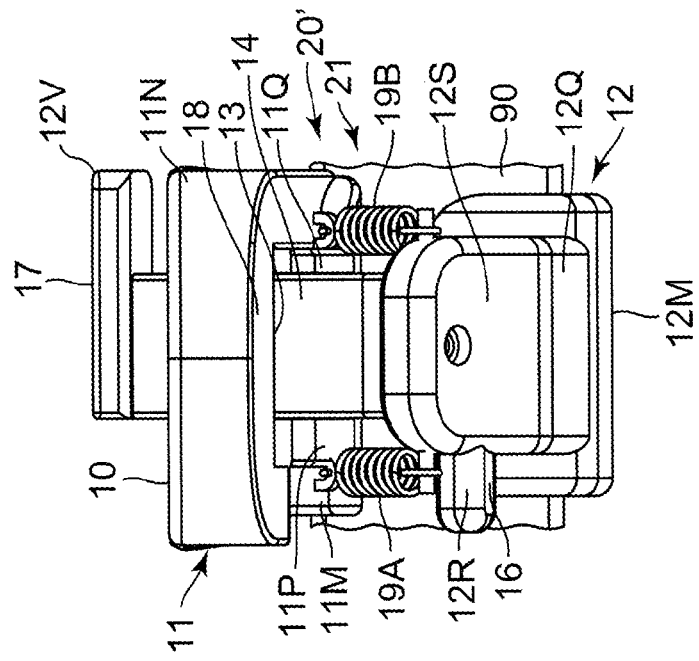
FIG. 13(B) is a diagram showing a view from the right side of the blood pressure monitor shown in FIG. 13(A).
Figure 13A:
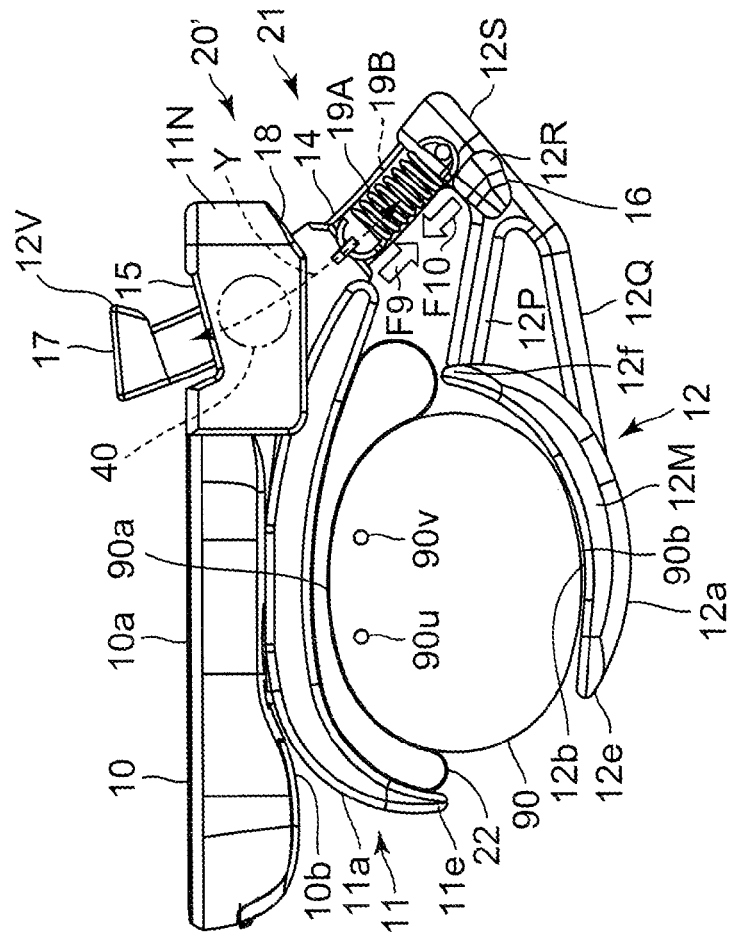
FIG. 13(A) is a perspective view showing a state (attached state) in which the blood pressure monitor including the blood pressure measurement cuff shown in FIG. 11 is attached to the left wrist serving as the measurement site.

With the blood pressure monitor 1', in the attached state (FIGS. 13(A) and 13(B)) resulting from performing the above-described three operations (f) to (h) in sequence, the measurement subject performs the following operation (i) of instructing the start of measurement.

(i) The measure/stop switch 52A serving as the operation switch provided on the main body 10 is pressed to input a blood pressure measurement start instruction to the main body 10. Accordingly, the fluid bladder 22 provided along the inner circumferential surface 11b of the first clamp portion 11M is inflated, and blood pressure measurement is performed (the flow of blood pressure measurement is the same as that described regarding the blood pressure monitor 1).

During blood pressure measurement, the attached state is reliably maintained, similarly to the description regarding the blood pressure monitor 1. Also, in the attached state, due to the tensile forces of the coil springs 19A and 19B, the fluid bladder 22 provided on the inner circumferential surface 11b of the first clamp portion 11M and the inner circumferential surface 12b of the second clamp portion 12M are closely adhered to the left wrist 90. Accordingly, blood pressure measurement is performed accurately and smoothly.

After the blood pressure measurement, the blood pressure monitor 1 is removed with the following operations (j) and (k).

(j) After measurement ends, as shown in FIG. 12(A), the measurement subject slides the first clamp portion 11M along the slide bar 14 toward the leading end of the slide bar 14 so as to slightly open the gap between the first clamp portion 11M and the second clamp portion 12M. This slight opening operation (j) can be easily performed by applying forces F7 and F8 against the tensile forces F9 and F10 of the coil springs 19A and 19B by pinching the third pressing region 17 and the fourth pressing region 18 with the thumb and another finger of the right hand so as to bring them close to each other, similarly to the first opening operation (e). Note that in the slight opening operation (j), the gap between the first clamp portion 11M and the second clamp portion 12M opens to such a degree that the latch mechanism 40 does not operate.

(k) While the gap between the first clamp portion 11M and the second clamp portion 12M is slightly open due to the forces F7 and F8, the measurement subject removes the left wrist 90 from the gap between the first clamp portion 11M and the second clamp portion 12M. In other words, the slight opening operation (j) and the removing operation (k) are performed simultaneously.

Thereafter, when the measurement subject removes the right hand from the cuff 20', the slide bar 14 slides with respect to the slide hole 13 in the direction of closing the gap between the first clamp portion 11M and the second clamp portion 12M due to the tensile forces F9 and F10 of the coil springs 19A and 19B, and the gap between the first clamp portion 11M and the second clamp portion 12M enters the closed state.

Note that instead of the slight opening operation (j), the latch mechanism 40 may open until the block portion 11N and the end plate portion 12V are engaged with each other, similarly to the first opening operation (f). In this case, after the removing operation (k), the forces F7 and F8 are applied against the tensile forces F9 and F10 of the coil springs 19A and 9B by pinching the third pressing region 17 and the fourth pressing region 18 with the thumb and another finger of the right hand again so as to bring them close to each other, and the engagement between the block portion 11N and the end plate portion 12V is canceled using the latch mechanism 40. Accordingly, the tensile forces F9 and F10 of the coil springs 19A and 19B are mitigated so as to retain the first clamp portion 11M and the second clamp portion 12M in the closed state.

With the above-described operation procedure, it was assumed that the blood pressure monitor 1' is attached to a measurement site belonging to the left half of the body (e.g., the left wrist), but there is no limitation to this. The blood pressure monitor 1' may be attached to a measurement site belonging to the right half of the body (e.g., the right wrist). In this case, the slide hole 13 and the slide bar 14 are arranged on the side near the center of the body of the measurement subject, and in this case, on the side near the left hand, in the periphery of the measurement site. In this case, the measurement subject can easily perform the operations with the left hand (one hand), similarly to the case of the blood pressure monitor 1.

Also, in the above example, the coil springs 19A and 19B are included as elastic members, but there is no limitation to this. The elastic members need only apply an elastic force in the direction of bringing the first clamp portion 11M and the second clamp portion 12M close to each other, and for example, may be rubber bands.

Also, in the above example, the latch mechanism 40 is included, but there is no limitation to this. The latch mechanism 40 may be omitted. In this case, while the gap between the first clamp portion 11M and the second clamp portion 12M is slightly open due to the forces F7 and F8, the measurement subject arranges the left wrist 90 between the first clamp portion 11M and the second clamp portion 12M. In other words, the first opening operation (f) and the arranging operation (g) are performed simultaneously.

Also, it is envisioned that the above-described blood pressure monitors 1 and 1' are attached to a wrist and thus have integrated shapes in which the main body 10 is integrally attached to the cuff 20 or 20', but there is no limitation to this. For example, it is also possible to use a type in which it is envisioned that the blood pressure monitor 1 or 1' is attached to an upper arm and thus the cuff 20 or 20' and the main body 10 are connected by an elongated flexible tube.

The above-described embodiments are merely examples, and various modifications are possible without departing from the scope of the invention. Also, the multiple above-described embodiments can be achieved independently or in combination with each other. Also, the various characteristics of different embodiments can be achieved independently or in combination with each other.

REFERENCE SIGNS LIST 1, 1' Blood pressure monitor
10 Main body
11 Upper-side member
11M First clamp portion
12 Lower-side member
12M Second clamp portion
13 Slide hole
13e1 First edge
13e2 Second edge
13e3 Third edge
13e4 Fourth edge
14 Slide bar
15 First pressing region
16 Second pressing region
17 Third pressing region
18 Fourth pressing region
20, 20' Cuff
21 Clamp mechanism
52 Operation unit

The invention claimed is:
1. A blood pressure measurement cuff including a clamp mechanism that sandwiches a substantially bar-shaped measurement site, wherein the clamp mechanism comprises:
a first clamp portion having a shape with a first curvature that is curved along a first half of an outer circumferential surface of the measurement site so as to press a side of the first half;
a second clamp portion having a shape with a second curvature that is curved along a second half opposite to the first half of the outer circumferential surface of the measurement site so as to press a side of the second half;
a slide hole that is formed at one end portion in a circumferential direction of the first clamp portion so as to penetrate in a penetration direction intersecting with the circumferential direction; and
a slide bar that extends from one end portion of the second clamp portion corresponding to the one end portion of the first clamp portion and into the slide hole of the first clamp portion, fits therein, and slides with friction with respect to the slide hole,
wherein other end portions of the first clamp portion and the second clamp portion each refer to an end portion on a side opposite to the one end portion among both end portions in the circumferential direction,
wherein the slide hole and the slide bar are curved with a third curvature such that a center portion of the third curvature is protruding towards a side near other end portions of the first clamp portion and the second clamp portion,
wherein the clamp mechanism is used for blood pressure measurement, and
wherein the first curvature and the second curvature are curved in a circumferential direction, while the third curvature has an opposite direction of curvature to the circumferential direction.

2. The blood pressure measurement cuff according to claim 1,
wherein a fluid bladder that is to be inflated during blood pressure measurement is provided along one or both of an inner circumferential surface of the first clamp portion and an inner circumferential surface of the second clamp portion.

3. The blood pressure measurement cuff according to claim 1,
wherein a first pressing region for placing a finger is formed adjacent to the slide hole on the outer circumferential surface side of the one end portion of the first clamp portion, and
wherein a second pressing region for placing a finger is formed at a position corresponding to the first pressing region on the outer circumferential surface side of the one end portion of the second clamp portion.

4. The blood pressure measurement cuff according to claim 1,
wherein a third pressing region for placing a finger is formed on a leading end of the slide bar, and
wherein a fourth pressing region for placing a finger is formed adjacent to the slide hole on the inner circumferential surface side of the one end portion of the first clamp portion.

5. The blood pressure measurement cuff according to claim 1,
wherein the cross section of the slide hole taken orthogonally to the penetration direction is substantially rectangular.

6. The blood pressure measurement cuff according to claim 5,
wherein among edges constituting an exit/entrance of the slide hole on a side away from the second clamp portion in the penetration direction, a second edge on a side near the other end portion of the first clamp portion is at a position closer to the second clamp portion in the penetration direction than a first edge on a side away from the other end portion of the first clamp portion is, and/or
wherein among edges constituting an exit/entrance on a side near the second clamp portion of the slide hole in the penetration direction, a third edge on a side far from the other end portion of the first clamp portion is at a position farther from the second clamp portion in the penetration direction than a fourth edge on a side near the other end portion of the first clamp portion is.

7. The blood pressure measurement cuff according to claim 6,
wherein curves are formed in cross sections of the first edge and the fourth edge so as to reduce friction, and
wherein cross sections of the second edge and the third edge are formed in right angles or acute angles so as to increase friction.

8. The blood pressure measurement cuff according to claim 1,
wherein a dimension in the circumferential direction of the second clamp portion is set to be smaller than a dimension in the circumferential direction of the first clamp portion, and
wherein the penetration direction of the slide hole is directed outward in the circumferential direction with respect to the one end portion of the first clamp portion as the inner circumferential surface side is approached from the outer circumferential surface side of the first clamp portion.

9. The blood pressure measurement cuff according to claim 8,
wherein a fluid bladder that is to be inflated during blood pressure measurement is provided in approximately the entire region along the inner circumferential surface of the first clamp portion, and
wherein an element that restricts swelling of an opposing portion of the fluid bladder is provided on an inner circumferential surface side of a portion adjacent to the one end portion of the second clamp portion.

10. The blood pressure measurement cuff according to claim 1, comprising:
an elastic member that applies a tensile force between the one end portion of the first clamp portion and the one end portion of the second clamp portion.

11. The blood pressure measurement cuff according to claim 10, comprising:
a latch mechanism that keeps the first clamp portion and the second clamp portion in an open state.

* * * * *